(12) United States Patent
Delgado et al.

(10) Patent No.: US 10,443,070 B2
(45) Date of Patent: Oct. 15, 2019

(54) NUCLEIC ACID MOLECULES THAT CONTROL PATHOGENS

(71) Applicant: Dow AgroSciences LLC, Indianapolis, IN (US)

(72) Inventors: Javier A. Delgado, Indianapolis, IN (US); Justin M. Lira, Zionsville, IN (US); Chaoxian Geng, Zionsville, IN (US); Tony K. Trullinger, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/880,882

(22) Filed: Jan. 26, 2018

(65) Prior Publication Data

US 2018/0216130 A1  Aug. 2, 2018

Related U.S. Application Data

(60) Provisional application No. 62/452,517, filed on Jan. 31, 2017.

(51) Int. Cl.
*C12N 15/82* (2006.01)
*C12N 15/113* (2010.01)

(52) U.S. Cl.
CPC ........ *C12N 15/8282* (2013.01); *C12N 15/113* (2013.01); *C12N 15/8218* (2013.01)

(58) Field of Classification Search
None
See application file for complete search history.

(56) References Cited

U.S. PATENT DOCUMENTS

2016/0215290 A1* 7/2016 Kogel ................ C12N 15/1137

OTHER PUBLICATIONS

Skinner et al, 1998, Curr Genet, 34:393-398.*
Avenot et al, 2010, Crop Protection, 643-651.*

* cited by examiner

*Primary Examiner* — Jason Deveau Rosen

(57) ABSTRACT

This disclosure concerns nucleic acid molecules and methods of use thereof for control of pathogens through RNA interference-mediated inhibition of target coding and transcribed non-coding sequences in pathogens. The disclosure also concerns methods for applying dsRNA through formulations and/or transgenic plants that express nucleic acid molecules useful for the control of pathogens, and the plant cells and plants obtained thereby.

16 Claims, No Drawings
Specification includes a Sequence Listing.

SEQUENCE LISTING

<160> NUMBER OF SEQ ID NOS: 32

<210> SEQ ID NO 1
<211> LENGTH: 1247
<212> TYPE: DNA
<213> ORGANISM: Zymoseptoria tritici

<400> SEQUENCE: 1

```
ctctccactc ttctcacata ccacacaatg gctcttcgac tcgcgacgag gcgctttgcg      60
ccaattgcct tccgccgcgg aatggccacc acgatcgagc acaccaagga gcctatctcc     120
gccaccgccg aggcactctc cgcctcgcgg cctcctatca aggaaacgaa gacgtcgacc     180
gtcaaggagc cacagatgga cgccgatgcg aagacaaaga ccttccacat ctaccgatgg     240
aaccccgatc agcccaccga caagcccgc atgcagtcat acacgctgga cctgaacaag     300
acgggtccta tgatgttgga tgctctgatc aggatcaaga acgaggtgga cccgaccttg     360
acattccgaa ggagttgcag agagggtatt tgcggcagct gtgccatgaa catcgacggc     420
gtcaacacat tggcgtgttt gtgtgagtag tggacaaaag atgcatcggg ccagttcggg     480
aactgacgat ttggcaggcc gcattccac cgacacagca aaggagactc gcatttaccc     540
acttccacac acctacgtcg tcaaggacct cgtgccagac atgacccagt tctacaagca     600
gtacaagtcc atcaagccat acctccagcg cgacaccgca ccaccagatg tatgcaccat     660
ccttcacctt cccatacttg atctcctgac tgacacatcc acttgcaggg caaagagaat     720
cgtcagtccg tcgccgatcg caagaagctt gatggtcttt acgagtgcat tctctgcgca     780
tgctgcagca catcttgccc atcctactgg tggaactcgg aggagtacct cggaccagct     840
```

```
gtccttctcc agtcataccg atggatcaac gactcgcgtg acgagaagac cgcacagcgc    900
aaggacgcac tcaacaacag catgagcttg taccgatgcc acaccattct gaattgctca    960
aggacctgcc ccaagggctt gaaccccgct ttggccatcg cggagatcaa gaagagcatg   1020
gctttcacgg gatagatgga acgagatgat tggaaagcgg ggagttgagg aacgggatct   1080 gttttttgcgt gctggcatcg cctagatttg tcccagtcaa gagggagcag ttgtgccgat   1140
tttgcggcat tgtggcaatc agtgagccac ggttctatcg tttcatgtgt aaatagcaat   1200
tgcatttgcg gctgtctcga aatcgacgga agacatttta caacata              1247
```

<210> SEQ ID NO 2
<211> LENGTH: 297
<212> TYPE: PRT
<213> ORGANISM: Zymoseptoria tritici

<400> SEQUENCE: 2

```
Met Ala Leu Arg Leu Ala Thr Arg Arg Phe Ala Pro Ile Ala Phe Arg
1               5                   10                  15

Arg Gly Met Ala Thr Thr Ile Glu His Thr Lys Glu Pro Ile Ser Ala
            20                  25                  30

Thr Ala Glu Ala Leu Ser Ala Ser Arg Pro Pro Ile Lys Glu Thr Lys
        35                  40                  45

Thr Ser Thr Val Lys Glu Pro Gln Met Asp Ala Asp Ala Lys Thr Lys
    50                  55                  60

Thr Phe His Ile Tyr Arg Trp Asn Pro Asp Gln Pro Thr Asp Lys Pro
65                  70                  75                  80

Arg Met Gln Ser Tyr Thr Leu Asp Leu Asn Lys Thr Gly Pro Met Met
                85                  90                  95

Leu Asp Ala Leu Ile Arg Ile Lys Asn Glu Val Asp Pro Thr Leu Thr
            100                 105                 110

Phe Arg Arg Ser Cys Arg Glu Gly Ile Cys Gly Ser Cys Ala Met Asn
        115                 120                 125

Ile Asp Gly Val Asn Thr Leu Ala Cys Leu Cys Arg Ile Pro Thr Asp
    130                 135                 140

Thr Ala Lys Glu Thr Arg Ile Tyr Pro Leu Pro His Thr Tyr Val Val
145                 150                 155                 160

Lys Asp Leu Val Pro Asp Met Thr Gln Phe Tyr Lys Gln Tyr Lys Ser
                165                 170                 175

Ile Lys Pro Tyr Leu Gln Arg Asp Thr Ala Pro Pro Asp Gly Lys Glu
            180                 185                 190

Asn Arg Gln Ser Val Ala Asp Arg Lys Lys Leu Asp Gly Leu Tyr Glu
        195                 200                 205

Cys Ile Leu Cys Ala Cys Cys Ser Thr Ser Cys Pro Ser Tyr Trp Trp
    210                 215                 220

Asn Ser Glu Glu Tyr Leu Gly Pro Ala Val Leu Leu Gln Ser Tyr Arg
225                 230                 235                 240

Trp Ile Asn Asp Ser Arg Asp Glu Lys Thr Ala Gln Arg Lys Asp Ala
                245                 250                 255

Leu Asn Asn Ser Met Ser Leu Tyr Arg Cys His Thr Ile Leu Asn Cys
            260                 265                 270

Ser Arg Thr Cys Pro Lys Gly Leu Asn Pro Ala Leu Ala Ile Ala Glu
        275                 280                 285

Ile Lys Lys Ser Met Ala Phe Thr Gly
    290                 295
```

<210> SEQ ID NO 3
<211> LENGTH: 894
<212> TYPE: DNA
<213> ORGANISM: Zymoseptoria tritici

<400> SEQUENCE: 3

```
atggctcttc gactcgcgac gaggcgcttt gcgccaattg ccttccgccg cggaatggcc      60
accacgatcg agcacaccaa ggagcctatc tccgccaccg ccgaggcact ctccgcctcg     120
cggcctccta tcaaggaaac gaagacgtcg accgtcaagg agccacagat ggacgccgat     180
gcgaagacaa agaccttcca catctaccga tggaaccccg atcagccac cgacaagccc      240
cgcatgcagt catacacgct ggacctgaac aagacgggtc ctatgatgtt ggatgctctg     300
atcaggatca agaacgaggt ggacccgacc ttgacattcc gaaggagttg cagagagggt     360
atttgcggca gctgtgccat gaacatcgac ggcgtcaaca cattggcgtg tttgtgccgc     420
attcccaccg acacagcaaa ggagactcgc atttacccac ttccacacac ctacgtcgtc     480
aaggacctcg tgccagacat gacccagttc tacaagcagt acaagtccat caagccatac     540
ctccagcgcg acaccgcacc accagatggc aaagagaatc gtcagtccgt cgccgatcgc     600
aagaagcttg atggtcttta cgagtgcatt ctctgcgcat gctgcagcac atcttgccca     660
tcctactggt ggaactcgga ggagtacctc ggaccagctg tccttctcca gtcataccga     720
tggatcaacg actcgcgtga cgagaagacc gcacagcgca aggacgcact caacaacagc     780
atgagcttgt accgatgcca caccattctg aattgctcaa ggacctgccc caagggcttg     840
aaccccgctt tggccatcgc ggagatcaag aagagcatgg ctttcacggg atag          894
```

<210> SEQ ID NO 4
<211> LENGTH: 721
<212> TYPE: DNA
<213> ORGANISM: Zymoseptoria tritici

<400> SEQUENCE: 4

```
catttcccca tccacctaca agaaagccaa ccccaacgca ctcgcaacac tcaaccccac      60
aaccgtccac cccgtcgtct gcacctgctt attcgtaatc atactcgccg tatcccacac     120
caaatgcctc actccattca cgaatgaaa cgtcaccggc aacgccaaaa tcgtcttggt      180
caagacctgc aacaggaccg gccaggcgcc gaaagaggcc gcgagggcgg cggactcgag     240
gtgccaacct agagatggcg cggcgaggta gaggagtccg aaggcgtaga aggctcccga     300
ggcggcgacg cccgtgacgc ggttgagggc cgagaggtac caggttattt gcggtttgta     360
gattgcgagg tggggcgcga cggggcggtt gaggcgttgt ttggcgagga tttcgttgcg     420
ggcgtgggat tcgagacgg cggctgctgt tacttggctg ttgagggat gtgagtgggg      480
gatggagaga ggaggaggtg ggaggataga tggtcttacc ggcgctgctg ttggaaggag     540
ttgttgccga gggcgatggc ggcggggggtt gcgaagcgga gggtggaggg ttggagggct     600
actgttggag gttggagtgg ttagtgacta ggacgatagc agcggagggt ggagggacgg     660
taagaagacg tacaccgccg aagcgactgc tgggtgagct tctgtgccaa catcgtgaga     720
c                                                                    721
```

<210> SEQ ID NO 5
<211> LENGTH: 187
<212> TYPE: PRT
<213> ORGANISM: Zymoseptoria tritici -continued

<400> SEQUENCE: 5

```
Met Leu Ala Gln Lys Leu Thr Gln Gln Ser Leu Arg Arg Leu Ala Leu
1               5                   10                  15

Gln Pro Ser Thr Leu Arg Phe Ala Thr Pro Ala Ala Ile Ala Leu Gly
            20                  25                  30

Asn Asn Ser Phe Gln Gln Gln Arg Arg Gln Val Thr Ala Ala Ala Val
        35                  40                  45

Ser Glu Ser His Ala Arg Asn Glu Ile Leu Ala Lys Gln Arg Leu Asn
    50                  55                  60

Arg Pro Val Ala Pro His Leu Ala Ile Tyr Lys Pro Gln Ile Thr Trp
65                  70                  75                  80

Tyr Leu Ser Ala Leu Asn Arg Val Thr Gly Val Ala Ala Ser Gly Ala
                85                  90                  95

Phe Tyr Ala Phe Gly Leu Leu Tyr Leu Ala Ala Pro Ser Leu Gly Trp
            100                 105                 110

His Leu Glu Ser Ala Ala Leu Ala Ala Ser Phe Gly Ala Trp Pro Val
        115                 120                 125

Leu Leu Gln Val Leu Thr Lys Thr Ile Leu Ala Leu Pro Val Thr Phe
    130                 135                 140

His Ser Leu Asn Gly Val Arg His Leu Val Trp Asp Thr Ala Ser Met
145                 150                 155                 160

Ile Thr Asn Lys Gln Val Gln Thr Thr Gly Trp Thr Val Val Gly Leu
                165                 170                 175

Ser Val Ala Ser Ala Leu Gly Leu Ala Phe Leu
            180                 185
```

<210> SEQ ID NO 6
<211> LENGTH: 564
<212> TYPE: DNA
<213> ORGANISM: Zymoseptoria tritici

<400> SEQUENCE: 6

```
atgttggcac agaagctcac ccagcagtcg cttcggcggt tagccctcca accctccacc      60
ctccgcttcg caaccccgc cgccatcgcc ctcggcaaca actccttcca acagcagcgc      120
cgccaagtaa cagcagccgc cgtctccgaa tcccacgccc gcaacgaaat cctcgccaaa      180
caacgcctca accgccccgt cgcgccccac ctcgcaatct acaaaccgca aataacctgg      240
tacctctcgg ccctcaaccg cgtcacgggc gtcgccgcct cgggagcctt ctacgccttc      300
ggactcctct acctcgccgc gccatctcta ggttggcacc tcgagtccgc cgccctcgcg      360
gcctctttcg gcgcctggcc ggtcctgttg caggtcttga ccaagacgat tttggcgttg      420
ccggtgacgt ttcattcgtt gaatggagtg aggcatttgg tgtgggatac ggcgagtatg      480
attacgaata agcaggtgca gacgacgggg tggacggttg tggggttgag tgttgcgagt      540
gcgttggggt tggctttctt gtag                                             564
```

<210> SEQ ID NO 7
<211> LENGTH: 750
<212> TYPE: DNA
<213> ORGANISM: Zymoseptoria tritici

<400> SEQUENCE: 7

```
catctttcgc aacatcccag cttctccatc tacaacttct gctcaatctt attcttcgca      60
tccttcgccg tcgcacccgc cgtccaaacc cgagcaatac ccgcagtcaa accaatatcg      120
ttcgtctcga attcgtacca tccccagcca accaggaaga cagcagcgac gttggcccag      180
```

```
tcggcgagct tgcgggtttt gggcacgcgc catgagggga agtagtcggt gatggcggat    240
ctggcgaata tgtcagaatg atacgggtgg gaagctgatg cgcatgtcgt actggaaacc    300
aatgtaagag tggatgataa tcatgccaat gaaagtgccg tccaaaaccg ggttgagcga    360
gccagcagcg aagggacaa tagtcaatgg gatgagagcc gcggagacga gtctgcatat    420
cctatatcag catccatacc tcatccttca cttgcgacaa catttcccta cctctccatc    480
gtccaatggt agcttccatg cgatggactc ggctctttca ccggcgccgg gtcattgaca    540
cctccacgga tgacttgcgg aagaggaggg agaataggtc tccgcgcagt ggtctggaag    600
ccggagcgct gggtgaattg agtgcggagg agggatgcgg cggggagggt ggaggcgcgc    660
ttggtggtgg ttgcggtgag gagctggcgg agagcagcgg ggcggagggc ggtggaggcc    720
atggcgacgg tgagggtgag tggagggtgg                                    750
```

<210> SEQ ID NO 8
<211> LENGTH: 193
<212> TYPE: PRT
<213> ORGANISM: Zymoseptoria tritici

<400> SEQUENCE: 8

```
Met Ala Ser Thr Ala Leu Arg Pro Ala Ala Leu Arg Gln Leu Leu Thr
1               5                  10                  15

Ala Thr Thr Thr Lys Arg Ala Ser Thr Leu Pro Ala Ala Ser Leu Leu
            20                  25                  30

Arg Thr Gln Phe Thr Gln Arg Ser Gly Phe Gln Thr Thr Ala Arg Arg
        35                  40                  45

Pro Ile Leu Pro Pro Leu Pro Gln Val Ile Arg Gly Gly Val Asn Asp
    50                  55                  60

Pro Ala Pro Val Lys Glu Pro Ser Pro Ser His Gly Ser Tyr His Trp
65                  70                  75                  80

Thr Met Glu Arg Leu Val Ser Ala Ala Leu Ile Pro Leu Thr Ile Val
                85                  90                  95

Pro Phe Ala Ala Gly Ser Leu Asn Pro Val Leu Asp Gly Thr Phe Ile
            100                 105                 110

Gly Met Ile Ile Ile His Ser Tyr Ile Gly Phe Gln Ser Ala Ile Thr
        115                 120                 125

Asp Tyr Phe Pro Ser Trp Arg Val Pro Lys Thr Arg Lys Leu Ala Asp
    130                 135                 140

Trp Ala Asn Val Ala Ala Val Phe Leu Val Gly Trp Gly Trp Tyr Glu
145                 150                 155                 160

Phe Glu Thr Asn Asp Ile Gly Leu Thr Ala Gly Ile Ala Arg Val Trp
                165                 170                 175

Thr Ala Gly Ala Thr Ala Lys Asp Ala Lys Asn Lys Ile Glu Gln Lys
            180                 185                 190

Leu
```

<210> SEQ ID NO 9
<211> LENGTH: 582
<212> TYPE: DNA
<213> ORGANISM: Zymoseptoria tritici

<400> SEQUENCE: 9

```
atggcctcca ccgccctccg ccccgctgct ctccgccagc tcctcaccgc aaccaccacc     60
aagcgcgcct ccaccctccc cgccgcatcc ctcctccgca ctcaattcac ccagcgctcc    120
```

| | |
|---|---|
| ggcttccaga ccactgcgcg agacctatt ctccctcctc ttccgcaagt catccgtgga | 180 |
| ggtgtcaatg acccggcgcc ggtgaaagag ccgagtccat cgcatggaag ctaccattgg | 240 |
| acgatggaga gactcgtctc cgcggctctc atcccattga ctattgtccc cttcgctgct | 300 |
| ggctcgctca acccggtttt ggacggcact ttcattggca tgattatcat ccactcttac | 360 |
| attggtttcc aatccgccat caccgactac ttcccctcat ggcgcgtgcc caaaacccgc | 420 |
| aagctcgccg actgggccaa cgtcgctgct gtcttcctgg ttggctgggg atggtacgaa | 480 |
| ttcgagacga acgatattgg tttgactgcg ggtattgctc gggtttggac ggcgggtgcg | 540 |
| acggcgaagg atgcgaagaa taagattgag cagaagttgt ag | 582 |

<210> SEQ ID NO 10
<211> LENGTH: 250
<212> TYPE: DNA
<213> ORGANISM: Zymoseptoria tritici

<400> SEQUENCE: 10

| | |
|---|---|
| aggcgctttg cgccaattgc cttccgccgc ggaatggcca ccacgatcga gcacaccaag | 60 |
| gagcctatct ccgccaccgc cgaggcactc tccgcctcgc ggcctcctat caaggaaacg | 120 |
| aagacgtcga ccgtcaagga gccacagatg gacgccgatg cgaagacaaa gaccttccac | 180 |
| atctaccgat ggaaccccga tcagcccacc gacaagcccc gcatgcagtc atacacgctg | 240 |
| gacctgaaca | 250 |

<210> SEQ ID NO 11
<211> LENGTH: 250
<212> TYPE: DNA
<213> ORGANISM: Zymoseptoria tritici

<400> SEQUENCE: 11

| | |
|---|---|
| cgagtgcatt ctctgcgcat gctgcagcac atcttgccca tcctactggt ggaactcgga | 60 |
| ggagtacctc ggaccagctg tccttctcca gtcataccga tggatcaacg actcgcgtga | 120 |
| cgagaagacc gcacagcgca aggacgcact caacaacagc atgagcttgt accgatgcca | 180 |
| caccattctg aattgctcaa ggacctgccc caagggcttg aaccccgctt tggccatcgc | 240 |
| ggagatcaag | 250 |

<210> SEQ ID NO 12
<211> LENGTH: 250
<212> TYPE: DNA
<213> ORGANISM: Zymoseptoria tritici

<400> SEQUENCE: 12

| | |
|---|---|
| cagcagtcgc ttcggcggtt agccctccaa ccctccaccc tccgcttcgc aaccccgcc | 60 |
| gccatcgccc tcggcaacaa ctccttccaa cagcagcgcc gccaagtaac agcagccgcc | 120 |
| gtctccgaat cccacgcccg caacgaaatc ctcgccaaac aacgcctcaa ccgcccgtc | 180 |
| gcgccccacc tcgcaatcta caaaccgcaa ataacctggt acctctcggc cctcaaccgc | 240 |
| gtcacgggcg | 250 |

<210> SEQ ID NO 13
<211> LENGTH: 250
<212> TYPE: DNA
<213> ORGANISM: Zymoseptoria tritici

<400> SEQUENCE: 13

| | |
|---|---|
| ctacgccttc ggactcctct acctcgccgc gccatctcta ggttggcacc tcgagtccgc | 60 |

```
cgccctcgcg gcctctttcg gcgcctggcc ggtcctgttg caggtcttga ccaagacgat 120
tttggcgttg ccggtgacgt ttcattcgtt gaatggagtg aggcatttgg tgtgggatac 180
ggcgagtatg attacgaata agcaggtgca gacgacgggg tggacggttg tggggttgag 240
tgttgcgagt 250

<210> SEQ ID NO 14
<211> LENGTH: 250
<212> TYPE: DNA
<213> ORGANISM: Zymoseptoria tritici
<400> SEQUENCE: 14
cccgctgctc tccgccagct cctcaccgca accaccacca agcgcgcctc caccctcccc 60
gccgcatccc tcctccgcac tcaattcacc cagcgctccg gcttccagac cactgcgcgg 120
agacctattc tccctcctct tccgcaagtc atccgtggag gtgtcaatga cccggcgccg 180
gtgaaagagc cgagtccatc gcatggaagc taccattgga cgatggagag actcgtctcc 240
gcggctctca 250

<210> SEQ ID NO 15
<211> LENGTH: 250
<212> TYPE: DNA
<213> ORGANISM: Zymoseptoria tritici
<400> SEQUENCE: 15
caacccggtt ttggacggca ctttcattgg catgattatc atccactctt acattggttt 60
ccaatccgcc atcaccgact acttcccctc atggcgcgtg cccaaaaccc gcaagctcgc 120
cgactgggcc aacgtcgctg ctgtcttcct ggttggctgg ggatggtacg aattcgagac 180
gaacgatatt ggtttgactg cgggtattgc tcgggtttgg acggcgggtg cgacggcgaa 240
ggatgcgaag 250

<210> SEQ ID NO 16
<211> LENGTH: 898
<212> TYPE: DNA
<213> ORGANISM: Puccinia graminis
<400> SEQUENCE: 16
atgtcactga agacacccgg ctcgggtgct ctcgagcttt ggccggggag ggcagaccat 60
cccagcaccc ccatcctcag aatcaagaca acagaccaca aacaacaaaa catcaaccgg 120
atcatcatgt cggccactcg tctatccacc ctgtcacgtc ccatgaacaa gctgcccatt 180
atcaaccgac tggcgctcat gacccctcaa taccgtcgat tgtcgaccag ctcgacgtca 240
tattcacaac cctcccctat cgtcaaggca gactcggccg cagatgcccc ctacgttagg 300
ggcacaatca acgaccctac tacctttcca ccacccagca aagcccacgg atcgattcat 360
tggaccttcg agagatcggt tgccgccagc ttgatcccgc tctcggccgc cactgctatt 420
tccagtgcca atccaattct tgacggggtc atcggggtat tcttgattgc ccattctcac 480
atgggattcg atcaatgctt ggtcgattat gttcccaaac gtaaattccc tgtgatcagc 540
ccgatcgcca cttggaccct acgagcatta acgtgcggcg ttctcgttgg agtgtaccaa 600
ttcaacacgc acgacatcgg tatgaccgag ttgatcaaga aggcatggaa ggcttgaaca 660
gaagaaatgg ggacgataat ttagaacttt tctcggtcgt ctcagttgat caccgtcaaa 720
cgttacactg aaaccttcat ttagaactta atctgactct catccttgtc tgctcataca 780
```

```
agtatcatca tgtttgtttt tgtcatcttt gtacagcaat caatcgattt tcatccaatc      840
ctcttttcag tcttgtcttc aactcaatca gacatccatc cattgaaaag ctgtttgg        898
```

```
<210> SEQ ID NO 17
<211> LENGTH: 250
<212> TYPE: DNA
<213> ORGANISM: Artificial Sequence
<220> FEATURE:
<223> OTHER INFORMATION: synthesized partial coding region
<400> SEQUENCE: 17
tgtagaaatc cttcagctcg gggccgtact tggcgaagca ctgggcgccg taggtcaggg      60
tggtcaccag ggtgctccag ggcacgggca catcgccggt ggtgcagatg aactgggcat     120
ccaccttgcc cacgctggca tcgccgtagc ccttgccgcg gatgctgaag gtgtggccat     180
ccacattgcc ctccatctcc accacgtagg ggatcttgcc gtggaacagc agggcgccgc     240
tggagcccat                                                            250
```

```
<210> SEQ ID NO 18
<211> LENGTH: 1247
<212> TYPE: RNA
<213> ORGANISM: Zymoseptoria tritici
<400> SEQUENCE: 18
cucuccacuc uucucacaua ccacacaaug gcucuucgac ucgcgacgag gcgcuuugcg      60
ccaauugccu uccgccgcgg aauggccacc acgaucgagc acaccaagga gccuaucucc     120
gccaccgcca aggcacucuc cgccucgcgg ccuccuauca aggaaacgaa gacgucgacc     180
gucaaggagc cacagaugga cgccgaugcg aagacaaaga ccuuccacau cuaccgaugg     240
aaccccgauc agcccaccga caagcccgc augcagucau acacgcugga ccugaacaag     300
acggguccua ugauguugga ugcucugauc aggaucaaga acgaggugga cccgaccuug     360
acauuccgaa ggaguugcag agaggguauu ugcggcagcu gugccaugaa caucgacggc     420
gucaacacau uggcguguuu gugugaguag uggacaaaag augcaucggg ccaguucggg     480
aacugacgau uuggcaggcc gcauucccac cgacacagca aaggagacuc gcauuuaccc     540
acuuccacac accuacgucg ucaaggaccu cgugccagac augacccagu ucuacaagca     600
guacaagucc aucaagccau accuccagcg cgacaccgca ccaccagaug uaugcaccau     660
ccuucaccuu cccauacuug aucuccugac ugacacaucc acuugcaggg caaagagaau     720 cgucagucg ucgccgaucg caagaagcuu gauggucuuu acgagugcau ucucugcgca     780
ugcugcagca caucuugccc auccuacugg uggaacucgg aggaguaccu cggaccagcu     840
guccuucucc agucuaccg auggaucaac gacucgcgug acgagaagac cgcacagcgc     900
aaggacgcac ucaacaacag caugagcuug uaccgaugcc acaccauucu gaauugcuca     960
aggaccugcc caagggcuu gaaccccgcu uuggccaucg cggagaucaa gaagagcaug    1020
gcuuucacgg gauagaugga acgagaugau uggaaagcgg ggaguugagg aacgggaucu    1080
guuuuugcgu gcuggcaucg ccuagauuug ucccagucaa gagggagcag uugugccgau    1140
uuugcggcau uguggcaauc agugagccac gguucuaucg uuucaugugu aaauagcaau    1200
ugcauuugcg gcugucucga aaucgacgga agacauuuua caacaua              1247
```

```
<210> SEQ ID NO 19
<211> LENGTH: 894
<212> TYPE: RNA
<213> ORGANISM: Zymoseptoria tritici
```

<400> SEQUENCE: 19
auggcucuuc gacucgcgac gaggcgcuuu gcgccaauug ccuuccgccg cggaauggcc 60
accacgaucg agcacaccaa ggagccuauc uccgccaccg ccgaggcacu cuccgccucg 120
cggccuccua ucaaggaaac gaagacgucg accgucaagg agccacagau ggacgccgau 180
gcgaagacaa agaccuucca caucuaccga uggaaccccg aucagcccac cgacaagccc 240
cgcaugcagu cauacacgcu ggaccugaac aagacggguc cuaugauguu ggaugcucug 300
aucaggauca agaacgaggu ggacccgacc uugacauucc gaaggaguug cagagagggu 360
auuugcggca gcugugccau gaacaucgac ggcgucaaca cauuggcgug uuugugccgc 420
auucccaccg acacagcaaa ggagacucgc auuuacccac uuccacacac cuacgucguc 480
aaggaccucg ugccagacau gacccaguuc uacaagcagu acaaguccau caagccauac 540
cuccagcgcg acaccgcacc accagauggc aaagagaauc gucaguccgu cgccgaucgc 600
aagaagcuug auggucuuua cgagugcauu cucugcgcau gcugcagcac aucuugccca 660
uccuacuggu ggaacucgga ggaguaccuc ggaccagcug uccuucucca gucauaccga 720
uggaucaacg acucgcguga cgagaagacc gcacagcgca aggacgcacu caacaacagc 780
augagcuugu accgaugcca caccauucug aauugcucaa ggaccugccc caagggcuug 840
aaccccgcuu uggccaucgc ggagaucaag aagagcaugg cuuucacggg auag 894

<210> SEQ ID NO 20
<211> LENGTH: 721
<212> TYPE: RNA
<213> ORGANISM: Zymoseptoria tritici
<400> SEQUENCE: 20
cauuucccca uccaccuaca agaaagccaa ccccaacgca cucgcaacac ucaaccccac 60
aaccguccac cccgucgucu gcaccugcuu auucguaauc auacucgccg uaucccacac 120
caaaugccuc acuccauuca acgaaugaaa cgucaccggc aacgccaaaa ucgucuuggu 180
caagaccugc aacaggaccg gccaggcgcc gaaagaggcc gcgagggcgg cggacucgag 240
gugccaaccu agagauggcg cggcgaggua gaggaguccg aaggcguaga aggcucccga 300
ggcggcgacg cccgugacgc gguugagggc cgagagguac cagguuauuu gcgguuugua 360
gauugcgagg uggggcgcga cggggcgguu gaggcguugu uuggcgagga uuucguugcg 420
ggcgugggau ucggagacgg cggcugcugu uacuuggcug uuggagggau gugaguggggg 480
gauggagaga ggaggaggug ggaggauaga uggucuuacc ggcgcugcug uuggaaggag 540
uuguugccga gggcgauggc ggcgggggguu gcgaagcgga ggguggaggg uuggagggcu 600
acuguuggag guuggagugg uuagugacua ggacgauagc agcggagggu ggagggacgg 660
uaagaagacg uacaccgccg aagcgacugc ugggugagcu ucugugccaa caucgugaga 720
c 721

<210> SEQ ID NO 21
<211> LENGTH: 564
<212> TYPE: RNA
<213> ORGANISM: Zymoseptoria tritici
<400> SEQUENCE: 21
auguuggcac agaagcucac ccagcagucg cuucggcggu uagcccucca acccuccacc 60
cuccgcuucg caaccccgc cgccaucgcc cucggcaaca acuccuucca acagcagcgc 120

-continued

| | |
|---|---|
| cgccaaguaa cagcagccgc cgucuccgaa ucccacgccc gcaacgaaau ccucgccaaa | 180 |
| caacgccuca accgccccgu cgcgccccac cucgcaaucu acaaaccgca aauaaccugg | 240 |
| uaccucucgg cccucaaccg cgucacgggc gucgccgccu cgggagccuu cuacgccuuc | 300 |
| ggacuccucu accucgccgc gccaucucua gguuggcacc ucgagcccgc cgccccgcg | 360 |
| gccucuuucg gcgccuggcc ggucuguug caggucuuga ccaagacgau uuggcguug | 420 |
| ccggugacgu ucauucguu gaauggagug aggcauuugg ugggauac ggcgaguaug | 480 |
| auuacgaaua agcaggugca gacgacgggg uggacgguug uggguugag uguugcgagu | 540 |
| gcguuggggu uggcuuucuu guag | 564 |

<210> SEQ ID NO 22
<211> LENGTH: 750
<212> TYPE: RNA
<213> ORGANISM: Zymoseptoria tritici

<400> SEQUENCE: 22

| | |
|---|---|
| caucuuucgc aacaucccag cuucuccauc uacaacuucu gcucaaucuu auucuucgca | 60 |
| uccuucgccg ucgcacccgc cguccaaacc cgagcaauac ccgcagucaa accaauaucg | 120 |
| uucgucucga auucguacca uccccagcca accaggaaga cagcagcgac guuggcccag | 180 |
| ucggcgagcu ugcggguuuu ggcacgcgc caugagggga aguagucggu gauggcggau | 240 |
| cuggcgaaua gucagaaug auacggguggg gaagcugaug cgcaugucgu acuggaaacc | 300 |
| aauguaagag uggaugauaa ucaugccaau gaaagugccg uccaaaaccg gguugagcga | 360 |
| gccagcagcg aagggacaa uagucaaugg gaugagagcc gcgagacga gucugcauau | 420 |
| ccuauaucag cauccauacc ucauccuuca cuugcgacaa cauuucccua ccucuccauc | 480 |
| guccaauggu agcuuccaug cgauggacuc ggcucuuuca ccggcgccgg gucauugaca | 540 |
| ccuccacgga ugacuugcgg aagaggaggg agaauagguc uccgcgcagu ggucuggaag | 600 |
| ccggagcgcu gggugaauug agucgggagg agggaugcgg cggggagggu ggaggcgcgc | 660 |
| uuggugguggg uucggugag gagcuggcgg agagcagcgg ggcggagggc gguggaggcc | 720 |
| auggcgacgg ugagggugag uggagggugg | 750 |

<210> SEQ ID NO 23
<211> LENGTH: 582
<212> TYPE: RNA
<213> ORGANISM: Zymoseptoria tritici

<400> SEQUENCE: 23

| | |
|---|---|
| auggccucca ccgccuccg ccccgcugcu cuccgccagc uccucaccgc aaccaccacc | 60 |
| aagcgcgccu ccaccucucc cgccgcaucc cucuccgca cucaauucac ccagcgcucc | 120 |
| ggcuuccaga ccacugcgcg gagaccuauu cucccuccuc uuccgcaagu cauccgugga | 180 |
| ggugucaaug acccggcgcc ggugaaagag ccgaguccau cgcauggaag cuaccauugg | 240 |
| acgauggaga gacucgucuc cgcggcucuc aucccauuga cuauugugccc uucgcugcu | 300 |
| ggcucgcuca acccgguuuu ggacggcacu ucauuggca ugauuaucau ccacucuuac | 360 |
| auugguuucc aauccgccau caccgacuac uucccccucau ggcgcugcc caaaacccgc | 420 |
| aagcucgccg acugggccaa cgucgcugcu gucuuccugg uuggcugggg augguacgaa | 480 |
| uucgagacga acgauauugg uuugacgcgc gguauugcuc ggguuggac ggcggguggcg | 540 |
| acggcgaagg augcgaagaa uaagauugag cagaaguugu ag | 582 |

-continued

```
<210> SEQ ID NO 24
<211> LENGTH: 250
<212> TYPE: RNA
<213> ORGANISM: Zymoseptoria tritici
<400> SEQUENCE: 24
aggcgcuuug cgccaauugc cuuccgccgc ggaauggcca ccacgaucga gcacaccaag 60
gagccuaucu ccgccaccgc cgaggcacuc uccgccucgc ggccuccuau caaggaaacg 120
aagacgucga ccgucaagga gccacagaug gacgccgaug cgaagacaaa gaccuuccac 180
aucuaccgau ggaaccccga ucagcccacc gacaagcccc gcaugcaguc auacacgcug 240
gaccugaaca 250

<210> SEQ ID NO 25
<211> LENGTH: 250
<212> TYPE: RNA
<213> ORGANISM: Zymoseptoria tritici
<400> SEQUENCE: 25
cgagugcauu cucugcgcau gcugcagcac aucuugccca uccuacuggu ggaacucgga 60
ggaguaccuc ggaccagcug uccuucucca gucauaccga uggaucaacg acucgcguga 120
cgagaagacc gcacagcgca aggacgcacu caacaacagc augagcuugu accgaugcca 180
caccauucug aauugcucaa ggaccugccc caagggcuug aaccccgcuu uggccaucgc 240
ggagaucaag 250

<210> SEQ ID NO 26
<211> LENGTH: 250
<212> TYPE: RNA
<213> ORGANISM: Zymoseptoria tritici
<400> SEQUENCE: 26
cagcagucgc uucggcgguu agcccuccaa cccuccaccc uccgcuucgc aaccccccgcc 60
gccaucgccc ucggcaacaa cuccuuccaa cagcagcgcc gccaaguaac agcagccgcc 120
gucuccgaau cccacgcccg caacgaaauc cucgccaaac aacgccucaa ccgccccguc 180
gcgccccacc ucgcaaucua caaaccgcaa auaaccuggu accucucggc ccucaaccgc 240
gucacgggcg 250

<210> SEQ ID NO 27
<211> LENGTH: 250
<212> TYPE: RNA
<213> ORGANISM: Zymoseptoria tritici
<400> SEQUENCE: 27
cuacgccuuc ggacuccucu accucgccgc gccaucucua gguuggcacc ucgaguccgc 60
cgcccucgcg gccucuuucg gcgccuggcc gguccuguug caggucuuga ccaagacgau 120
uuuggcguug ccggugacgu uucauucguu gaauggagug aggcauuugg ugugggauac 180
ggcgaguaug auuacgaaua agcaggugca gacgacgggg uggacgguug ugggguugag 240
uguugcgagu 250

<210> SEQ ID NO 28
<211> LENGTH: 250
<212> TYPE: RNA
<213> ORGANISM: Zymoseptoria tritici

<400> SEQUENCE: 28
```

| | | |
|---|---|---|
| cccgcugcuc uccgccagcu ccucaccgca accaccacca agcgcgccuc cacccuccccc | 60 | |
| gccgcauccc uccuccgcac ucaauucacc cagcgcuccg gcuuccagac cacugcgcgg | 120 | |
| agaccuauuc ucccuccucu uccgcaaguc auccguggag gugucaauga cccggcgccg | 180 | |
| gugaaagagc cgaguccauc gcauggaagc uaccauugga cgauggagag acucgucucc | 240 | |
| gcggcucuca | 250 | |

<210> SEQ ID NO 29
<211> LENGTH: 250
<212> TYPE: RNA
<213> ORGANISM: Zymoseptoria tritici

<400> SEQUENCE: 29

| | | |
|---|---|---|
| caacccgguu uuggacggca cuuucauugg caugauuauc auccacucuu acauuggguuu | 60 | |
| ccaauccgcc aucaccgacu acuuccccuc auggcgcgug cccaaaaccc gcaagcucgc | 120 | |
| cgacugggcc aacgucgcug cugucuuccu gguuggcugg ggaugguacg aauucgagac | 180 | |
| gaacgauauu gguuugacug cggguauugc ucggguuugg acggcgggug cgacggcgaa | 240 | |
| ggaugcgaag | 250 | |

<210> SEQ ID NO 30
<211> LENGTH: 898
<212> TYPE: RNA
<213> ORGANISM: Puccinia graminis

<400> SEQUENCE: 30

| | | |
|---|---|---|
| augucacuga agacacccgg cucggguugcu cucgagcuuu ggccggggag ggcagaccau | 60 | |
| cccagcaccc ccauccucag aaucaagaca acagaccaca aacaacaaaa caucaaccgg | 120 | |
| aucaucaugu cggccacucg ucuauccacc cugucacguc ccaugaacaa gcugcccauu | 180 | |
| aucaaccgac uggcgcucau gaccccucaa uaccgucgau ugucgaccag cucgacguca | 240 | |
| uauucacaac ccuccccuau cgucaaggca gacucggccg cagaugcccc cuacguuagg | 300 | |
| ggcacaauca acgacccuac uaccuuucca ccacccagca aagcccacgg aucgauucau | 360 | |
| uggaccuucg agagaucggu ugccgccagc uugauccccgc ucucgggccgc cacugcuauu | 420 | |
| uccagugcca auccaauucu ugacggggguc aucggguau ucuugauugc ccauucucac | 480 | |
| augggauucg aucaaugcuu ggucgauuau guucccaaac guaaauuccc ugugaucagc | 540 | |
| ccgaucgcca cuuggacccu acgagcauua acgugcggcg uucucguugg aguguaccaa | 600 | |
| uucaacacgc acgacaucgg uaugaccgag uugaucaaga aggcauggaa ggcuugaaca | 660 | |
| gaagaaaugg ggacgauaau uuagaacuuu ucucggucgu cucaguugau caccgucaaa | 720 | |
| cguuacacug aaaccuucau uuagaacuua aucugacucu cauccuuguc ugcucauaca | 780 | |
| aguaucauca uguuuguuuu ugucaucuuu guacagcaau caaucgauuu ucauccaauc | 840 | |
| cucuuuucag ucuugcuuc aacucaauca gacauccauc cauugaaaag cuguuugg | 898 | |

<210> SEQ ID NO 31
<211> LENGTH: 20
<212> TYPE: DNA
<213> ORGANISM: artificial sequence
<220> FEATURE:
<223> OTHER INFORMATION: NIa-1F PCR primer

<400> SEQUENCE: 31

| | | |
|---|---|---|
| ctggaccgat cggattaaga | 20 | |

```
<210> SEQ ID NO 32
<211> LENGTH: 20
<212> TYPE: DNA
<213> ORGANISM: artificial sequence
<220> FEATURE:
<223> OTHER INFORMATION: NIa-3R PCR primer

<400> SEQUENCE: 32
ctgagaactt ccatggcaca                                              20
```

NUCLEIC ACID MOLECULES THAT CONTROL PATHOGENS

CROSS REFERENCE TO RELATED APPLICATION

The present application claims priority to the benefit of U.S. Provisional Patent Application Ser. No. 62/452,517 filed Jan. 31, 2017 the disclosure of which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 27.9 KB ASCII (Text) file named "78911-US-NP-20180126-Sequence-Listing-ST25" created on Jan. 31, 2017.

TECHNICAL FIELD OF THE DISCLOSURE

The present disclosure relates generally to control of plant damage caused by pathogens. In particular embodiments, the present disclosure relates to identification of target coding and non-coding sequences, and the use of recombinant DNA technologies for post-transcriptionally repressing or inhibiting expression of target coding and non-coding sequences in the cells of a pathogen to provide a plant-protective effect.

BACKGROUND

A large amount of crop loss and plant damage is incurred each year due to plant diseases caused by two classes of fungi: Ascomycetes, causing a large number of leaf spots, blights, soil-born and post-harvest diseases; and Basidiomycetes, causing rust, smuts, bunts and soil born-diseases. Also, Oomycetes cause a number of plant diseases including downy mildews, leaf blights and soil-born diseases.

*Zymoseptoria tritici*, also known as *Septoria tritici*, also known as *Mycosphaerella graminicola*, also known as SEPTTR, is an ascomycete in the family Mycosphaerellaceae. This fungus, a species of filamentous fungus, is a wheat plant pathogen that causes *Septoria* leaf blotch. *Septoria* leaf blotch is difficult to control due to the development of resistance to multiple fungicides.

*Zymoseptoria tritici* infects its host through the stomata. There is a long latent period of up to two weeks following infection before symptoms develop (Orton, E. S. et. al., (2011) *Mycosphaerella graminicola*: from genomics to disease control. Molecular Plant Pathology 12(5):413-424). The fungus evades host defenses during the latent phase, followed by a rapid switch to necrotrophy immediately prior to symptom expression 12-20 days after penetration.

Wheat yields can be reduced by 30-50% due to losses caused by *Septoria* leaf blotch (STB) with a huge economic impact (Eyal, Z. et. al., (1987) The *Septoria* Diseases of Wheat: Concepts and Methods of Disease Management. Mexico, DF: CIMMYT). Global costs for fungicides to manage STB total hundreds of millions of dollars each year (Hardwick, N. V. et. al., (2001) Factors affecting diseases of winter wheat in England and Wales, 1989-98. Plant Pathol 50: 453-462; McDougall, P. (2006) Phillips McDougall Agriservice Report. Scotland, UK: Pathhead, Midlothian).

The control of phytopathogenic microorganisms, and in particular, fungi, is of vast economic importance since fungal growth on plants or on parts of plants inhibits production of foliage, fruit or seed, and the overall quality of a cultivated crop. Because of the economic ramifications of fungal propagation in agricultural and horticultural cultivations, a broad spectrum of fungicidal and fungistatic products has been developed for general and specific applications. Fungicides can be separated into two categories according to their fungicidal activity: protectants and curatives. Protectant fungicides, as the name implies, protect the plant against infection. A protectant fungicide must be applied before the pathogen lands on the plant surface and/or the infection process begins. Conversely, a curative fungicide must be able to halt disease development after the infection process has begun. A curative fungicide can be applied after the infection process has begun. Most curative fungicides also have protectant activity.

Inorganic fungicides were generally the first to be used in large-scale crop protection aimed against pathogenic fungi. Notable among these are elemental sulfur applied in powder form, and copper sulfate applied in caustic calcium aqueous mixture. While these inorganic fungicides are generally effective, they have significant drawbacks. The fungicides or derivatives of the fungicides are often environmentally non-recyclable. Additionally, pathogens often develop resistance to synthetic pesticides. Because of the development of resistance, continuous endeavors are needed to develop new crop protecting agents.

A variety of simple structured antimicrobial compounds have been developed. Notable among these are fungicide compositions based on copper, zinc or manganese that have been shown to be effective against a broad range of plant pathogenic fungi and bacteria. Fungicides in this category, unlike the category of inorganic fungicides previously discussed, are generally environmentally friendly and the microbes tend to not develop immunity against them. In certain applications, however, the use of these traditional inorganic fungicides for soil treatment is limited due to the absorption of the metal ions to soil particles.

A need, therefore, remains for antimicrobial compositions that are environmentally safe, cost affordable, and that are highly effective for controlling plant microbes, such as fungi, yeast and bacteria.

RNA interference (RNAi) is a process utilizing endogenous cellular pathways, whereby an interfering RNA (iRNA) molecule (e.g., a dsRNA molecule) that is specific for all, or any portion of adequate size, of a target gene sequence results in the degradation of the mRNA encoded thereby. In recent years, RNAi has been used to perform gene "knockdown" in a number of species and experimental systems; for example, *Caenorhabditis elegans*, plants, fungi, insect embryos, and cells in tissue culture. See, e.g., Fire et al. (1998) Nature 391:806-811; Martinez et al. (2002) Cell 110:563-574; McManus and Sharp (2002) Nature Rev. Genetics 3:737-747; Koch and Kogel (2014) Plant Biotech. J. 12:821-831.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro ribonucleic acid (miRNA) molecules may be similarly incorporated into RISC. Post-transcriptional gene silencing occurs when the guide strand binds specifically to a complementary sequence of an mRNA molecule and induces cleavage by Argonaute, the catalytic component of the RISC complex. This process is known to spread systemically throughout some eukaryotic organisms, despite initially limited concentrations of siRNA and/or miRNA, such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein. In fungi, there are two DICER enzymes, where DICER2 is the major enzyme participating in post-transcriptional gene silencing. On the other hand, DICER1 has a redundant role in the pathway (Catalanotto. C., et al., (2004) Redundancy of the two dicer genes in transgene-induced posttranscriptional gene silencing in *Neurospora crassa*. Molecular Cell Biology 24:2536-2545).

SUMMARY OF THE DISCLOSURE

Disclosed herein are nucleic acid molecules (e.g., target genes, DNAs, dsRNAs, siRNAs, shRNA, miRNAs, and hpRNAs), and methods of use thereof, for the control of pathogens, including, for example, *Zymoseptoria tritici* Desm.; *Zymoseptoria citri; Zymoseptoria caryae; Zymoseptoria curcurbitacearum; Zymoseptoria dianthi; Zymoseptoria glycines; Zymoseptoria helianthi; Zymoseptoria ostryae; Puccinia triticina; Puccinia striiformis* f. sp. *tritici; Phaeosphaeria nodorum; Rhyncosporium commune; Alternaria solani; Cercospora beticola; Magnaporthe grisea; Venturia inaequalis*; and *Phakopsora pachyrhizi*. In particular examples, exemplary nucleic acid molecules are disclosed that may be homologous to at least a portion of one or more native nucleic acid sequences in *Zymoseptoria*.

In these and further examples, the native nucleic acid sequence may be a target gene, the product of which may be, for example and without limitation: involved in a metabolic process, detoxification process, or structural development. In some examples, post-translational inhibition of the expression of a target gene by a nucleic acid molecule comprising a sequence homologous thereto may be lethal in the pathogen, or result in reduced growth and/or development. In specific examples of succinate dehydrogenase (Sdh), the gene has been shown to code the only enzyme involved in both the citric acid cycle and the electron transport chain. Sdh has gene subunits, which include but are not limited to gene subunits B (SdhB), C (SdhC), and D (SdhD). The SDH enzyme also catalyzes the oxidation of succinate to fumarate in the mitochondria matrix and transfers electrons to ubiquinone without pumping protons across the mitochondrial inner membrane. (Shaobai Huang, A Harvey Millar, Succinate dehydrogenase: the complex roles of a simple enzyme, Current Opinion in Plant Biology, Volume 16, Issue 3, June 2013, Pages 344-349, ISSN1369-5266). In particular examples, a target gene useful for post-transcriptional inhibition is the novel gene referred to herein as Sdh. An isolated nucleic acid molecule comprising a nucleotide sequence of Sdh (SEQ ID NO:1, SEQ ID NO:3, SEQ ID NO:4, SEQ ID NO:6, SEQ ID NO:7, SEQ ID NO:9); the complement of Sdh (SEQ ID NO:1, SEQ ID NO:3, SEQ ID NO:4, SEQ ID NO:6, SEQ ID NO:7, SEQ ID NO:9); and fragments of any of the foregoing is therefore disclosed herein. An isolated nucleic acid of the present disclosure may be operably linked operably to a heterologous promoter.

Also disclosed are nucleic acid molecules comprising a nucleotide sequence that encodes a polypeptide that is at least 85% identical to an amino acid sequence within a target gene product (for example, the product of a gene referred to as SDH). For example, a nucleic acid molecule may comprise a nucleotide sequence encoding a polypeptide that is at least 85% identical to an amino acid sequence of SEQ ID NOs:2, 5, 8 (SDH protein). In particular examples, a nucleic acid molecule comprises a nucleotide sequence encoding a polypeptide that is at least 85% identical to an amino acid sequence within a product of SDHB. In some embodiments, the nucleic acid molecule is a double-stranded nucleic acid. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, shRNA, miRNA, and hpRNA) molecules that are complementary to all or part of a pathogen target gene, for example: Sdh. In particular examples, cDNA molecules are disclosed that may be used to produce iRNA molecules that are complementary to all or part of Sdh (e.g., SEQ ID NO:1, SEQ ID NO:3, SEQ ID NO:4, SEQ ID NO:6, SEQ ID NO:7, SEQ ID NO:9).

Further disclosed are means for inhibiting expression of an essential gene in a pathogen, and means for protecting a plant from pathogens. A means for inhibiting expression of an essential gene in a pathogen is a single- or double-stranded RNA molecule consisting of at least one of SEQ ID NO:10 (*Zymoseptoria* Sdh subunit B-T1, herein sometimes referred to as sdhb-T1), SEQ ID NO:11 (*Zymoseptoria* Sdh subunit B-T2, herein sometimes referred to as sdhb-T2), SEQ ID NO:12 (*Zymoseptoria* Sdh subunit C, herein sometimes referred to as sdhc-T1), SEQ ID NO:13 (*Zymoseptoria* Sdh subunit C, herein sometimes referred to as sdhc-T2), SEQ ID NO:14 (*Zymoseptoria* Sdh subunit D, herein sometimes referred to as sdhd-T1), SEQ ID NO:15 (*Zymoseptoria* Sdh subunit D, herein sometimes referred to as sdhd-T2), or the complement thereof. Functional equivalents of means for inhibiting expression of an essential gene in a pathogen include single- or double-stranded RNA molecules that are substantially homologous to all or part of a *Zymoseptoria* gene or subunit comprising SEQ ID NO:1, SEQ ID NO:3, SEQ ID NO:4, SEQ ID NO:6, SEQ ID NO:7, or SEQ ID NO:9.

Disclosed are methods for controlling phytopathogens, comprising contacting a phytopathogen with an iRNA (e.g., dsRNA, siRNA, shRNA, miRNA, and hpRNA) molecule that functions upon being taken up by (e.g., ingested, absorbed, translocated within, or taken up by) the pathogen to inhibit a biological function within the pathogen, wherein the iRNA molecule comprises all or part of a nucleotide sequence selected from the group consisting of: SEQ ID NO:1, SEQ ID NO:3, SEQ ID NO:4, SEQ ID NO:6, SEQ ID NO:7, SEQ ID NO:9, and SEQ ID NOs:10-15; the complement of SEQ ID NO:1, SEQ ID NO:3, SEQ ID NO:4, SEQ ID NO:6, SEQ ID NO:7, SEQ ID NO:9, and SEQ ID NOs:10-15; a native coding sequence of a *Zymoseptoria* organism comprising all or part of any of SEQ ID NO:1, SEQ ID NO:3, SEQ ID NO:4, SEQ ID NO:6, SEQ ID NO:7, SEQ ID NO:9, and SEQ ID NOs:10-15; the complement of a native coding sequence of a *Zymoseptoria* organism comprising all or part of any of SEQ ID NO:1, SEQ ID NO:3, SEQ ID NO:4, SEQ ID NO:6, SEQ ID NO:7, SEQ ID NO:9, and SEQ ID NOs:10-15; a native non-coding sequence of a *Zymoseptoria* organism that is transcribed into a native RNA molecule comprising all or part of any of SEQ ID NO:1, SEQ ID NO:3, SEQ ID NO:4, SEQ ID NO:6, SEQ ID NO:7, SEQ ID NO:9, and SEQ ID NOs:10-15; and the complement of a native non-coding sequence of a *Zymoseptoria* organism that is transcribed into a native RNA molecule comprising all or part of any of SEQ ID NO:1, SEQ ID NO:3, SEQ ID NO:4, SEQ ID NO:6, SEQ ID NO:7, SEQ ID NO:9, and SEQ ID NOs:10-15.

In these and further examples, the dsRNAs, siRNAs, shRNAs, miRNAs, and/or hpRNAs may be uptaken and/or contacted by the pathogen. Uptake and/or contact of dsRNAs, siRNA, shRNAs, miRNAs, and/or hpRNAs of the disclosure may then result in RNAi in the pathogen, which in turn may result in silencing of a gene essential for viability of the pathogen and leading ultimately to mortality. Thus, methods are disclosed wherein nucleic acid molecules comprising exemplary nucleic acid sequence(s) useful for control of phytopathogens are provided to a fungal plant pathogen. In particular examples, the pathogen controlled by use of nucleic acid molecules of the disclosure may be *Zymoseptoria*. The foregoing and other features are exemplified in the following Detailed Description of several embodiments.

SEQUENCE LISTING

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand and reverse complementary strand are understood as included by any reference to the displayed strand. In the accompanying sequence listing:

SEQ ID NO:1 shows a DNA sequence comprising sdhB (subunit B) from *Zymoseptoria tritici*.

SEQ ID NO:2 shows a partial amino acid sequence of a SDHB protein (subunit B) from *Zymoseptoria tritici*.

SEQ ID NO:3 shows a DNA sequence comprising sdhB (subunit B) mRNA from *Zymoseptoria tritici*.

SEQ ID NO:4 shows a DNA sequence comprising sdhC (subunit C) from *Zymoseptoria tritici*.

SEQ ID NO:5 shows a partial amino acid sequence of a SDHC protein (subunit C) from *Zymoseptoria tritici*.

SEQ ID NO:6 shows a DNA sequence of sdhC (subunit C) mRNA from *Zymoseptoria tritici*.

SEQ ID NO:7 shows a DNA sequence of sdhD (subunit D) from *Zymoseptoria tritici*.

SEQ ID NO:8 shows a partial amino acid sequence of a SDHD protein (subunit D) from *Zymoseptoria tritici*.

SEQ ID NO:9 shows a DNA sequence of sdhD (subunit D) mRNA from *Zymoseptoria tritici*.

SEQ ID NO:10 shows a DNA sequence of sdhb-T1 from *Zymoseptoria tritici* that was used for in vitro dsRNA synthesis.

SEQ ID NO:11 shows a DNA sequence of sdhb-T2 from *Zymoseptoria tritici* that was used for in vitro dsRNA synthesis.

SEQ ID NO:12 shows a DNA sequence of sdhc-T1 from *Zymoseptoria tritici* that was used for in vitro dsRNA synthesis.

SEQ ID NO:13 shows a DNA sequence of sdhc-T2 from *Zymoseptoria tritici* that was used for in vitro dsRNA synthesis.

SEQ ID NO:14 shows a DNA sequence of sdhd-T1 from *Zymoseptoria tritici* that was used for in vitro dsRNA synthesis.

SEQ ID NO:15 shows a DNA sequence of sdhd-T2 from *Zymoseptoria tritici* that was used for in vitro dsRNA synthesis.

SEQ ID NO:16 shows an mRNA sequence comprising sdh from *Puccinia graminis* f. sp. *tritici*.

SEQ ID NO:17 shows a DNA sequence of YFP.

SEQ ID NO:18 shows a RNA sequence comprising sdhB (subunit B) from *Zymoseptoria tritici*.

SEQ ID NO:19 shows a RNA sequence comprising sdhB (subunit B) mRNA from *Zymoseptoria tritici*.

SEQ ID NO:20 shows a RNA sequence of sdhC (subunit C) from *Zymoseptoria tritici*.

SEQ ID NO:21 shows a RNA sequence of sdhC (subunit C) mRNA from *Zymoseptoria tritici*.

SEQ ID NO:22 shows a RNA sequence of sdhD (subunit D) from *Zymoseptoria tritici*.

SEQ ID NO:23 shows a RNA sequence of sdhD (subunit D) mRNA from *Zymoseptoria tritici*.

SEQ ID NO:24 shows an RNA sequence of sdhb-T1 *Zymoseptoria tritici* that was used for in vitro dsRNA synthesis.

SEQ ID NO:25 shows an RNA sequence of sdhb-T2 *Zymoseptoria tritici* that was used for in vitro dsRNA synthesis.

SEQ ID NO:26 shows an RNA sequence of sdhc-T1 *Zymoseptoria tritici* that was used for in vitro dsRNA synthesis.

SEQ ID NO:27 shows an RNA sequence of sdhc-T2 *Zymoseptoria tritici* that was used for in vitro dsRNA synthesis.

SEQ ID NO:28 shows an RNA sequence of sdhd-T1 *Zymoseptoria tritici* that was used for in vitro dsRNA synthesis.

SEQ ID NO:29 shows an RNA sequence of sdhd-T2 *Zymoseptoria tritici* that was used for in vitro dsRNA synthesis.

SEQ ID NO:30 shows an RNA of the mRNA sequence comprising sdh from *Puccinia graminis* f. sp. *tritici*.

SEQ ID NO:31 shows a PCR primer for detection of the Nia sequence used in the transgene.

SEQ ID NO:32 shows a PCR primer for detection of the Nia sequence used in the transgene.

DETAILED DESCRIPTION

I. Overview of Several Embodiments

Disclosed herein are methods and compositions for control of fungal plant pathogen. Methods for improving the yield of a crop are also provided. In addition, methods for identifying one or more gene(s) essential to the lifecycle of a pathogen for use as a target gene for RNAi-mediated control of a pathogen population are provided. In some embodiments, methods are provided for post-transcriptional repression of expression or inhibition of a target gene via nucleic acid molecules that are complementary to a coding or non-coding sequence of the target gene in a pathogen. In these and further embodiments, a pathogen may uptake one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, shRNA, miRNA, and/or hpRNA that is complementary to coding and/or non-coding sequences of the target gene(s) to achieve at least partial control of a pathogen. Disclosed is a set of isolated and purified nucleic acid molecules comprising a nucleotide sequence, for example, as set forth in any of SEQ ID NO:1, SEQ ID NO:3, SEQ ID NO:4, SEQ ID NO:6, SEQ ID NO:7, SEQ ID NOs:9-15, and fragments thereof. In some embodiments, a stabilized dsRNA molecule may be expressed from this sequence, fragments thereof, or a gene comprising one of these sequences, for the post-transcriptional silencing or inhibition of a target gene. In certain embodiments, isolated and purified nucleic acid molecules comprise all or part of SEQ ID NO:1. In other embodiments, isolated and purified nucleic acid molecules comprise all or part of SEQ ID NO:3. In still further embodiments, isolated and purified nucleic acid molecules comprise all or part of SEQ ID NO:4. In other embodiments, isolated and purified nucleic acid molecules comprise all or part of SEQ ID NO:6. In other embodiments, isolated and purified nucleic acid molecules comprise all or part of SEQ ID NO:7. In yet other embodiments, isolated and purified nucleic acid molecules comprise all or part of SEQ ID NOs:9-15.

Particular embodiments involve a recombinant host cell having in its genome a recombinant DNA sequence encoding at least one iRNA (e.g., dsRNA) molecule(s) comprising all of SEQ ID NO:1, SEQ ID NO:3, SEQ ID NO:4, SEQ ID NO:6, SEQ ID NO:7, and/or SEQ ID NO:9, or a fragment thereof (e.g., SEQ ID NOs:10-15). When contacted by a pathogen, the iRNA molecule(s) may silence or inhibit the expression of a target gene comprising SEQ ID NO:1, SEQ ID NO:3, SEQ ID NO:4, SEQ ID NO:6, SEQ ID NO:7, and/or SEQ ID NO:9, or a fragment thereof (e.g., SEQ ID NOs:10-15), in the pathogen, and thereby result in cessation of growth, development, reproduction, and/or feeding in the pathogen.

Also disclosed herein are methods for delivery of control agents, such as an iRNA molecule, to a pathogen. Such control agents may cause, directly or indirectly, an impairment in the ability of the pathogen to feed, grow, or otherwise cause damage in a host. In some embodiments, a method is provided comprising delivery of a stabilized dsRNA molecule to a pathogen to suppress at least one target gene in the pathogen, thereby reducing or eliminating plant damage by a pathogen. In some embodiments, a method of inhibiting expression of a target gene in a pathogen may result in the cessation of growth, development, reproduction, and/or feeding in the pathogen. In some embodiments, the method may eventually result in death of the pathogen.

In some embodiments, compositions (e.g., a topical composition) are provided that comprise an iRNA (e.g., dsRNA) molecule of the disclosure for use in plants, animals, and/or the environment of a plant or animal to achieve the elimination or reduction of a pathogen infection. In particular embodiments, the composition may be a nutritional composition or food source to be uptaken by the pathogen. Some embodiments comprise making the nutritional composition or food source available to the pathogen. Uptake of a composition comprising iRNA molecules may result in the uptake of the molecules by one or more cells of the pathogen, which may in turn result in the inhibition of expression of at least one target gene in cell(s) of the pathogen. Uptake of or damage to a plant or plant cell by a pathogen may be limited or eliminated in or on any host tissue or environment in which the pathogen is present by providing one or more compositions comprising an iRNA molecule of the disclosure in the host of the pathogen.

In other embodiments, the composition may be a topical composition. Some embodiments comprise making the topical composition available to the pathogen. Contact of a composition comprising iRNA molecules may result in the uptake of the molecules by one or more cells of the pathogen, which may in turn result in the inhibition of expression of at least one target gene in cell(s) of the pathogen. Damage to a plant or plant cell by a pathogen may be limited or eliminated in or on any host tissue or environment in which the pathogen is present by providing one or more compositions comprising an iRNA molecule of the disclosure in the host of the pathogen.

II. Abbreviations dsRNA double-stranded ribonucleic acid
NCBI National Center for Biotechnology Information
gDNA genomic deoxyribonucleic acid
iRNA inhibitory ribonucleic acid
ORF open reading frame
RNAi ribonucleic acid interference
mRNA messenger ribonucleic acid
miRNA micro ribonucleic acid
shRNA small hairpin ribonucleic acid
siRNA small inhibitory ribonucleic acid
hpRNA hairpin ribonucleic acid
rRNA ribosomal RNA
UTR untranslated region
PCR polymerase chain reaction
RISC RNA-induced Silencing Complex
YFP yellow fluorescent protein
SEM standard error of the mean
WSMV wheat streak mosaic virus III. Terms In the description and tables which follow, a number of terms are used. In order to provide a clear and consistent understanding of the specification and claims, including the scope to be given such terms, the following definitions are provided:

Pathogen: As used herein, the term "pathogen" refers to fungus of the genus *Zymoseptoria, Mycosphaerella, Puccinia, Phaeosphaeria, Rhyncosporium, Alternaria, Cercospora, Magnaporthe, Venturia*, or *Phakopsora*, which infect wheat, corn, cotton, barley, tomato, sugar beet, cucumber, rice, apple, soybean, rye, oats, triticale, melons, member of Solanum family, and other true grasses. In particular examples, a pathogen is selected from the list comprising *Zymoseptoria tritici; Puccinia triticina; Phaeosphaeria nodorum; Rhyncosporium commune; Alternaria solani; Cercospora beticola; Magnaporthe grisea; Venturia inaequalis*; and *Phakopsora pachyrhizi*. In particular examples, a pathogen is selected from the list comprising *Zymoseptoria* also referred to herein as SEPTTR and *Septoria*.

Contact (with an organism): As used herein, the term "contact with" or "uptake by" an organism (e.g., a fungal pathogen), with regard to a nucleic acid molecule, includes internalization of the nucleic acid molecule into the organism, for example and without limitation: uptake of the molecule by the organism (e.g., by feeding); contacting the organism with a composition comprising the nucleic acid molecule; and soaking of organisms with a solution comprising the nucleic acid molecule.

Encoding a dsRNA: As used herein, the term "encoding a dsRNA" includes a gene whose RNA transcription product is capable of forming an intramolecular dsRNA structure or intermolecular dsRNA structure (e.g., by hybridizing to a target RNA molecule).

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern (RNA) blot, RT-PCR, western (immuno-) blot, or in vitro, in situ, or in vivo protein activity assay(s).

Genetic material: As used herein, the term "genetic material" includes all genes and nucleic acid molecules, such as DNA and RNA.

Inhibition: As used herein, the term "inhibition", when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

AT GAT GAT G polynucleotide
TAC TAC TAC "complement" of the polynucleotide
CAT CAT CAT "reverse complement" of the polynucleotide "Nucleic acid molecules" include single- and double-stranded forms of DNA (ssDNA and dsDNA, respectively); single-stranded forms of RNA (ssRNA); and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), shRNA (small hairpin RNA), miRNA (micro-RNA), hpRNA (hairpin RNA), tRNA (transfer RNA, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "polynucleotide" and "nucleic acid" and "fragments" thereof, or more generally "segment", will be understood by those in the art as a functional term that includes both genomic sequences, ribosomal RNA sequences, transfer RNA sequences, messenger RNA sequences, operon sequences, and smaller engineered nucleotide sequences that encode or may be adapted to encode peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a "primer", which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence", "structural nucleotide sequence", or "structural nucleic acid molecule" refers to a nucleotide sequence that is ultimately translated into a polypeptide, via transcription and mRNA, when placed under the control of appropriate regulatory sequences. With respect to RNA, the term "coding polynucleotide" refers to a polynucleotide that is translated into a peptide, polypeptide, or protein. Coding polynucleotides include, but are not limited to: genomic DNA; cDNA; EST; and recombinant nucleotide sequences. The boundaries of a coding sequence are determined by a translation start codon at the 5'-terminus and a translation stop codon at the 3'-terminus. Although a translation initiation codon can be 5'-AUG (in transcribed mRNA molecules; 5'-ATG in the corresponding DNA molecule), some genes, including mitochondrial genes, have a translation start codon having the RNA sequence 5'-GUG, 5'-UUG or 5'-CUG, 5'-AUA, 5'-ACG or 5'-CUG. Thus, the terms "translation initiation codon" and "start codon" can encompass many codon sequences. It is also known that eukaryotic and prokaryotic genes may have two or more alternative start codons, any one of which may be utilized for translation initiation in a particular cell type or tissue, or under a particular set of conditions. Therefore, "start codon" and "translation initiation codon" refer to the codon or codons that are used to initiate translation of an mRNA molecule transcribed from a gene, such as a mitochondrial gene, regardless of the sequence(s) of such codons. Similarly, "stop codon" and "translation termination codon" refer to the codon or codons that are used to terminate translation of an mRNA molecule transcribed from a gene, such as a mitochondrial gene, regardless of the sequence(s) of such codons.

As used herein, "transcribed non-coding polynucleotide" refers to at least one segment of an mRNA molecule such as 5'UTR, 3'UTR, and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18S rRNA, 23S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "linker" in a nucleic acid and which is transcribed into an RNA molecule.

Genome: As used herein, the term "genome" refers to chromosomal DNA found within the nucleus of a cell, and also refers to organelle DNA found within subcellular components of the cell. In some embodiments of the disclosure, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the disclosure, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity", as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-244; Higgins and Sharp (1989) CABIOS 5:151-153; Corpet et al. (1988) Nucleic Acids Res. 16:10881-10890; Huang et al. (1992) Comp. Appl. Biosci. 8:155-165; Pearson et al. (1994) Methods Mol. Biol. 24:307-331; Tatiana et al. (1999) FEMS Microbiol. Lett. 174:247-250. A detailed consideration of sequence alignment methods and homology calculations can be found in, e.g., Altschul et al. (1990) J. Mol. Biol. 215:403-410.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an antiparallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization will determine the stringency of hybridization. The ionic strength of the wash buffer and the wash temperature also influence stringency. Calculations regarding hybridization conditions required for attaining particular degrees of stringency are known to those of ordinary skill in the art, and are discussed, for example, in Sambrook et al. (ed.) Molecular Cloning: A Laboratory Manual, 2$^{nd}$ ed., vol. 1-3, Cold Spring Harbor Laboratory Press, Cold Spring Harbor, N.Y., 1989, chapters 9 and 11, and updates; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in Laboratory Techniques in Biochemistry and Molecular Biology-Hybridization with Nucleic Acid Probes, Part I, Chapter 2, Elsevier, N Y, 1993; and Ausubel et al., Eds., Current Protocols in Molecular Biology, Chapter 2, Greene Publishing and Wiley-Interscience, N Y, 1995, and updates.

As used herein, "stringent conditions" encompass conditions under which hybridization will occur only if there is more than 80% sequence match between the hybridization molecule and a homologous sequence within the target nucleic acid molecule. "Stringent conditions" include further particular levels of stringency. Thus, as used herein, "moderate stringency" conditions are those under which molecules with more than 80% sequence match (i.e. having less than 20% mismatch) will hybridize; conditions of "high stringency" are those under which sequences with more than 90% match (i.e. having less than 10% mismatch) will hybridize; and conditions of "very high stringency" are those under which sequences with more than 95% match (i.e. having less than 5% mismatch) will hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology", with regard to a contiguous nucleic acid sequence, refers to contiguous nucleotide sequences that are borne by nucleic acid molecules that hybridize under stringent conditions to a nucleic acid molecule having the reference nucleic acid sequence. For example, nucleic acid molecules having sequences that are substantially homologous to a reference nucleic acid sequence of SEQ ID NO:1 are those nucleic acid molecules that hybridize under stringent conditions (e.g., the Moderate Stringency conditions set forth, supra) to nucleic acid molecules having the reference nucleic acid sequence of SEQ ID NO:1. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Wheat plant: As used herein the term "wheat" or "wheat plant" refers to a plant of the genus, *Triticum*, for example, *T. aestivum, T. aethiopicum, T. araraticum, T. boeoticum, T. carthlicum, T. compactum, T. dicoccoides, T. dicoccon, T. durum, T. ispahanicum, T. karamyschevii, T. macha, T. militinae, T. monococcum, T. polonicum, T. spelta, T. sphaerococcum, T. timopheevii, T. turanicum, T. turgidum, T. urartu, T. vavilovii, T. zhukovskyi*.

Unless specifically indicated or implied, the terms "a", "an", and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's Genes X, Jones & Bartlett Publishers, 2009 (ISBN 10 0763766321); Krebs et al. (eds.), The Encyclopedia of Molecular Biology, Blackwell Science Ltd., 1994 (ISBN 0-632-02182-9); and Meyers R. A. (ed.), Molecular Biology and Biotechnology: A Comprehensive Desk Reference, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a *Zymoseptoria* Sequence

A. Overview

Described herein are nucleic acid molecules useful for the control of pathogens. Described nucleic acid molecules include target sequences (e.g., native genes, and non-coding sequences), dsRNAs, siRNAs, hpRNAs, shRNA, and miRNAs. For example, dsRNA, siRNA, shRNA, miRNA and/or hpRNA molecules are described in some embodiments that may be specifically complementary to all or part of one or more native nucleic acid sequences in a pathogen. In these and further embodiments, the native nucleic acid sequence(s) may be one or more target gene(s), the product of which may be, for example and without limitation: involved in a metabolic process; involved in a reproductive process; or involved in detoxification. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in pathogens, or result in reduced growth and/or reproduction.

In some embodiments, at least one target gene in a pathogen may be selected, wherein the target gene comprises a nucleotide sequence comprising Sdh (SEQ ID NO:1, SEQ ID NO:3, SEQ ID NO:4, SEQ ID NO:6, SEQ ID NO:7, SEQ ID NO:9), or a fragment thereof (e.g., SEQ ID NOs:10-15). In particular examples, a target gene in a pathogen is selected, wherein the target gene comprises a novel nucleotide sequence comprising Sdh (SEQ ID NO:1, SEQ ID NO:3, SEQ ID NO:4, SEQ ID NO:6, SEQ ID NO:7, SEQ ID NO:9) or a fragment thereof (e.g., SEQ ID NOs: 10-15).

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of a protein product of Sdh (SEQ ID NO:1, SEQ ID NO:3, SEQ ID NO:4, SEQ ID NO:6, SEQ ID NO:7, or SEQ ID NO:9). A target gene may be any nucleic acid sequence in a pathogen, the post-transcriptional inhibition of which has a deleterious effect on the pathogen, or provides a protective benefit against the pathogen to a plant. In particular examples, a target gene is a nucleic acid molecule comprising a nucleotide sequence that encodes a polypeptide comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of a protein product of novel nucleotide sequence SEQ ID NO:1, SEQ ID NO:3, SEQ ID NO:4, SEQ ID NO:6, SEQ ID NO:7, or SEQ ID NO:9.

Provided according to the disclosure are nucleotide sequences, the expression of which results in an RNA molecule comprising a nucleotide sequence that is specifically complementary to all or part of a native RNA molecule that is encoded by a coding sequence in a pathogen. In some embodiments, after uptake and/or contact of the expressed RNA molecule by a pathogen, down-regulation of the coding sequence in cells of the pathogen may be obtained. In particular embodiments, down-regulation of the coding sequence in cells of the pathogen may result in a deleterious effect on the growth, viability, proliferation, and/or reproduction of the pathogen.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target pathogen genes. Such sequences may be derived from both mono-cistronic and poly-cistronic genes.

Thus, also described herein in connection with some embodiments are iRNA molecules (e.g., dsRNAs, siRNAs, shRNA, miRNAs and hpRNAs) that comprise at least one nucleotide sequence that is specifically complementary to all or part of a target sequence in a pathogen. In some embodiments an iRNA molecule may comprise nucleotide sequence(s) that are complementary to all or part of a plurality of target sequences; for example, 2, 3, 4, 5, 6, 7, 8, 9, 10, or more target sequences. Also disclosed are cDNA sequences that may be used for the production of dsRNA molecules, siRNA molecules, shRNA molecules, miRNA molecules and/or hpRNA molecules that are specifically complementary to all or part of a target sequence in a pathogen.

In some embodiments, nucleic acid molecules useful for the control of pathogens may include: all or part of a native nucleic acid sequence isolated from *Zymoseptoria* comprising Sdh (SEQ ID NO:1, SEQ ID NO:3, SEQ ID NO:4, SEQ ID NO:6, SEQ ID NO:7, or SEQ ID NO:9); nucleotide sequences that when expressed result in an RNA molecule comprising a nucleotide sequence that is specifically complementary to all or part of a native RNA molecule that is encoded by Sdh (SEQ ID NO:1, SEQ ID NO:3, SEQ ID NO:4, SEQ ID NO:6, SEQ ID NO:7, or SEQ ID NO:9); iRNA molecules (e.g., dsRNAs, siRNAs, shRNA, miRNAs and hpRNAs) that comprise at least one nucleotide sequence that is specifically complementary to all or part of Sdh (SEQ ID NO:1, SEQ ID NO:3, SEQ ID NO:4, SEQ ID NO:6, SEQ ID NO:7, or SEQ ID NO:9); cDNA sequences that may be used for the production of dsRNA molecules, siRNA molecules, shRNA molecules, miRNA and/or hpRNA molecules that are specifically complementary to all or part of Sdh (SEQ ID NO:1, SEQ ID NO:3, SEQ ID NO:4, SEQ ID NO:6, SEQ ID NO:7, or SEQ ID NO:9); and recombinant DNA constructs.

B. Nucleic Acid Molecules

The present disclosure provides, inter alia, iRNA (e.g., dsRNA, siRNA, shRNA, miRNA, and hpRNA) molecules that inhibit target gene expression in a cell or tissue of a pathogen; and DNA molecules capable of being expressed as an iRNA molecule in a cell or microorganism to inhibit target gene expression in a cell or tissue of a pathogen.

Some embodiments of the disclosure provide an isolated nucleic acid molecule comprising at least one (e.g., one, two, three, or more) nucleotide sequence(s) selected from the group consisting of: SEQ ID NO:1; the complement of SEQ ID NO:1; SEQ ID NO:3; the complement of SEQ ID NO:3; SEQ ID NO:4; the complement of SEQ ID NO:4; SEQ ID NO:6; the complement of SEQ ID NO:6; SEQ ID NO:7; the complement of SEQ ID NO:7; SEQ ID NO:9; the complement of SEQ ID NO:9; a fragment of at least 15 contiguous nucleotides (e.g., 15, 16, 17, 18, 19, 20, 21, 22, 23, 24, 25, 26, 27, 28, 29, 30 or more contiguous nucleotides) of any of SEQ ID NO:1, SEQ ID NO:3, SEQ ID NO:4, SEQ ID NO:6, SEQ ID NO:7, and SEQ ID NO:9 (e.g., SEQ ID NOs:10-15); the complement of a fragment of at least 15 contiguous nucleotides of any of SEQ ID NO:1, SEQ ID NO:3, SEQ ID NO:4, SEQ ID NO:6, SEQ ID NO:7, and SEQ ID NO:9; a native coding sequence of a pathogenic organism (e.g., *Zymoseptoria*) comprising all or part of any of SEQ ID NO:1, SEQ ID NO:3, SEQ ID NO:4, SEQ ID NO:6, SEQ ID NO:7, and SEQ ID NO:9; the complement of a native coding sequence of a pathogenic organism comprising all or part of any of SEQ ID NO:1, SEQ ID NO:3, SEQ ID NO:4, SEQ ID NO:6, SEQ ID NO:7, and SEQ ID NO:9; a native non-coding sequence of a pathogenic organism that is transcribed into a native RNA molecule comprising all or part of any of SEQ ID NO:1, SEQ ID NO:3, SEQ ID NO:4, SEQ ID NO:6, SEQ ID NO:7, and SEQ ID NO:9; the complement of a native non-coding sequence of a pathogenic organism that is transcribed into a native RNA molecule comprising all or part of any of SEQ ID NO:1, SEQ ID NO:3, SEQ ID NO:4, SEQ ID NO:6, SEQ ID NO:7, and SEQ ID NO:9; a fragment of at least 15 contiguous nucleotides of a native non-coding sequence of a pathogenic organism that is transcribed into a native RNA molecule comprising all or part of any of SEQ ID NO:1, SEQ ID NO:3, SEQ ID NO:4, SEQ ID NO:6, SEQ ID NO:7, and SEQ ID NO:9; the complement of a fragment of at least 15 contiguous nucleotides of a native non-coding sequence of a pathogenic organism that is transcribed into a native RNA molecule comprising all or part of any of SEQ ID NO:1, SEQ ID NO:3, SEQ ID NO:4, SEQ ID NO:6, SEQ ID NO:7, and SEQ ID NO:9; a fragment of at least 15 contiguous nucleotides of a native coding sequence of a pathogenic organism that is transcribed into a native RNA molecule comprising SEQ ID NO:1, SEQ ID NO:3, SEQ ID NO:4, SEQ ID NO:6, SEQ ID NO:7, and SEQ ID NO:9; the complement of a fragment of at least 15 contiguous nucleotides of a native coding sequence of a pathogenic organism that is transcribed into a native RNA molecule comprising SEQ ID NO:1, SEQ ID NO:3, SEQ ID NO:4, SEQ ID NO:6, SEQ ID NO:7, and SEQ ID NO:9. In some embodiments of the disclosure, the isolated nucleic acid molecule comprises one or more of SEQ ID NOs:10-15. In particular embodiments, contact with or uptake by a fungal pathogen of the isolated nucleic acid sequence inhibits the growth, development, reproduction and/or feeding of the pathogen.

In some embodiments, a nucleic acid molecule of the disclosure may comprise at least one (e.g., one, two, three, or more) DNA sequence(s) capable of being expressed as an iRNA molecule in a cell or microorganism to inhibit target gene expression in a cell or tissue of a pathogen. In one embodiment, the at least one (e.g., one, two, three, or more) DNA sequence(s) may be derived from a polynucleotide(s) selected from the group consisting of: SEQ ID NO:1, SEQ ID NO:3, SEQ ID NO:4, SEQ ID NO:6, SEQ ID NO:7, and SEQ ID NO:9. Derivatives of SEQ ID NO:1, SEQ ID NO:3, SEQ ID NO:4, SEQ ID NO:6, SEQ ID NO:7, or SEQ ID NO:9 include fragments of SEQ ID NO:1, SEQ ID NO:3, SEQ ID NO:4, SEQ ID NO:6, SEQ ID NO:7, and SEQ ID NO:9. In some embodiments, such a fragment may comprise, for example, at least about 15 contiguous nucleotides of SEQ ID NO:1, SEQ ID NO:3, SEQ ID NO:4, SEQ ID NO:6, SEQ ID NO:7, or SEQ ID NO:9, or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NO:1, SEQ ID NO:3, SEQ ID NO:4, SEQ ID NO:6, SEQ ID NO:7, or SEQ ID NO:9, or a complement thereof. In these and further embodiments, such a fragment may comprise, for example, more than about 15 contiguous nucleotides of SEQ ID NO:1, SEQ ID NO:3, SEQ ID NO:4, SEQ ID NO:6, SEQ ID NO:7, or SEQ ID NO:9, or a complement thereof. Thus, a fragment of SEQ ID NO:1, SEQ ID NO:3, SEQ ID NO:4, SEQ ID NO:6, SEQ ID NO:7, or SEQ ID NO:9 may comprise, for example, 15, 16, 17, 18, 19, 20, 21, about 25, (e.g., 22, 23, 24, 25, 26, 27, 28, and 29), about 30, about 40, (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200 or more contiguous nucleotides of SEQ ID NO:1, SEQ ID NO:3, SEQ ID NO:4, SEQ ID NO:6, SEQ ID NO:7, or SEQ ID NO:9, or a complement thereof. In some specific embodiments the fragment is selected from the group consisting of SEQ ID NOs:10-15.

Some embodiments comprise introducing partial- or fully-stabilized dsRNA molecules into a pathogen to inhibit expression of a target gene in a cell or tissue of the pathogen. When expressed as an iRNA molecule (e.g., dsRNA, siRNA, shRNA, miRNA, and hpRNA) and taken up by a pathogen, nucleic acid sequences comprising one or more fragments of SEQ ID NO:1, SEQ ID NO:3, SEQ ID NO:4, SEQ ID NO:6, SEQ ID NO:7, or SEQ ID NO:9 (e.g., SEQ ID NOs:10-15) may cause one or more of death, growth inhibition, reduction in population size, and/or cessation of infection by a pathogen. For example, in some embodiments, a dsRNA molecule comprising a nucleotide sequence including about 15 to about 300 or about 19 to about 300 nucleotides that are substantially homologous to a pathogen target gene sequence and comprising one or more fragments of a nucleotide sequence comprising SEQ ID NO:1, SEQ ID NO:3, SEQ ID NO:4, SEQ ID NO:6, SEQ ID NO:7, or SEQ ID NO:9 is provided. Expression of such a dsRNA molecule may, for example, lead to mortality and/or growth inhibition in a pathogen that takes up the dsRNA molecule.

In certain embodiments, dsRNA molecules provided by the disclosure comprise nucleotide sequences complementary to a target gene comprising SEQ ID NO:1, SEQ ID NO:3, SEQ ID NO:4, SEQ ID NO:6, SEQ ID NO:7, or SEQ ID NO:9 and/or nucleotide sequences complementary to a fragment of SEQ ID NO:1, SEQ ID NO:3, SEQ ID NO:4, SEQ ID NO:6, SEQ ID NO:7, or SEQ ID NO:9, the inhibition of which target gene in a pathogen results in the reduction or removal of a protein or nucleotide sequence agent that is essential for the pathogen's growth, development, or other biological function. A selected nucleotide sequence may exhibit from about 80% to about 100% sequence identity to SEQ ID NO:1, SEQ ID NO:3, SEQ ID NO:4, SEQ ID NO:6, SEQ ID NO:7, or SEQ ID NO:9, a contiguous fragment of the nucleotide sequence set forth in SEQ ID NO:1, SEQ ID NO:3, SEQ ID NO:4, SEQ ID NO:6, SEQ ID NO:7, or SEQ ID NO:9, or the complement of either of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%;

about 94% about 95%; about 96%; about 97%; about 98%; about 98.5%; about 99%; about 99.5%; or about 100% sequence identity to SEQ ID NO:1, SEQ ID NO:3, SEQ ID NO:4, SEQ ID NO:6, SEQ ID NO:7, or SEQ ID NO:9, a contiguous fragment of the nucleotide sequence set forth in SEQ ID NO:1, SEQ ID NO:3, SEQ ID NO:4, SEQ ID NO:6, SEQ ID NO:7, or SEQ ID NO:9, or the complement of either of the foregoing.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target pathogen species, or the DNA molecule can be constructed as a chimera from a plurality of such specifically complementary sequences.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-498; and Hamilton and Baulcombe (1999) Science 286(5441):950-952. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in pathogens.

C. Obtaining Nucleic Acid Molecules

A variety of native sequences in pathogens may be used as target sequences for the design of nucleic acid molecules of the disclosure, such as iRNAs and DNA molecules encoding iRNAs. Selection of native sequences is not, however, a straight-forward process. Only a small number of native sequences in the pathogen will be effective targets. For example, it cannot be predicted with certainty whether a particular native sequence can be effectively down-regulated by nucleic acid molecules of the disclosure, or whether down-regulation of a particular native sequence will have a detrimental effect on the growth, viability, proliferation, and/or reproduction of the pathogen.

In some embodiments, nucleic acid molecules of the disclosure are selected to target cDNA sequences that encode proteins or parts of proteins essential for pathogen survival, such as amino acid sequences involved in metabolic or catabolic biochemical pathways, cell division, reproduction, energy metabolism, digestion, host plant recognition, and the like. As described herein, uptake or contact of compositions by a target organism containing one or more dsRNAs, at least one segment of which is specifically complementary to at least a substantially identical segment of RNA produced in the cells of the target organism, can result in the death or other inhibition of the target. A nucleotide sequence, either DNA or RNA, derived from a pathogen can be used to construct formulations to protect plants from infection by the pathogen. The host plant of the pathogen (e.g., wheat), for example, can be treated with one or more of the nucleotide sequences derived from the pathogen as provided herein. This may result in the suppression of expression of one or more genes in the cells of the pathogen, and ultimately death or inhibition of its growth or development.

Thus, in some embodiments, a gene is targeted that is essentially involved in the growth, development, and reproduction of a pathogen. Other target genes for use in the present disclosure may include, for example, those that play roles in pathogen viability, growth, development, infectivity, and reproduction. A target gene may therefore be a housekeeping gene or a transcription factor. Additionally, a native pathogen nucleotide sequence for use in the present disclosure may also be derived from a homolog (e.g., an ortholog), of a plant, viral, bacterial or insect gene, the function of which is known to those of skill in the art, and the nucleotide sequence of which is specifically hybridizable with a target gene in the genome of the target pathogen. Methods of identifying a homolog of a gene with a known nucleotide sequence by hybridization are known to those of skill in the art.

In some embodiments, the disclosure provides methods for obtaining a nucleic acid molecule comprising a nucleotide sequence for producing an iRNA (e.g., dsRNA, siRNA, shRNA, miRNA, and hpRNA) molecule. One such embodiment comprises: (a) analyzing one or more target gene(s) for their expression, function, and phenotype upon dsRNA-mediated gene suppression in a pathogen; (b) probing a cDNA or gDNA library with a probe comprising all or a portion of a nucleotide sequence or a homolog thereof from a targeted pathogen that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA sequence or a homolog thereof; and (f) chemically synthesizing all or a substantial portion of a gene sequence, or a siRNA or miRNA or shRNA or hpRNA or mRNA or dsRNA.

In further embodiments, a method for obtaining a nucleic acid fragment comprising a nucleotide sequence for producing a substantial portion of an iRNA (e.g., dsRNA, siRNA, shRNA, miRNA, and hpRNA) molecule includes: (a) synthesizing first and second oligonucleotide primers specifically complementary to a portion of a native nucleotide sequence from a targeted pathogen; and (b) amplifying a cDNA or gDNA insert present in a cloning vector using the first and second oligonucleotide primers of step (a), wherein the amplified nucleic acid molecule comprises a substantial portion of a siRNA or shRNA or miRNA or hpRNA or mRNA or dsRNA molecule.

Nucleic acids of the disclosure can be isolated, amplified, or produced by a number of approaches. For example, an iRNA (e.g., dsRNA, siRNA, shRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P. E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,415,732, 4,458,066, 4,725,677, 4,973,679, and 4,980,460. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present disclosure may be produced chemically or enzymatically by one skilled in the art through manual or automated reactions, or in vivo in a cell comprising a nucleic acid molecule comprising a sequence encoding the RNA, dsRNA, siRNA, miRNA, shRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., U.S. Pat. Nos. 5,593,874, 5,693,512, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the disclosure also provides a DNA molecule for introduction into a cell (e.g., a bacterial cell, a yeast cell, or a plant cell), wherein the DNA molecule comprises a nucleotide sequence that, upon expression to RNA and contact and/or uptake by a pathogen, achieves suppression of a target gene in a cell or tissue of the pathogen.

In specific embodiments, a recombinant DNA molecule of the disclosure may comprise a nucleic acid sequence encoding a dsRNA molecule. Such recombinant DNA molecules may encode dsRNA molecules capable of inhibiting the expression of endogenous target gene(s) in a pathogen cell upon contact and/or uptake.

In these and further embodiments, one strand of a dsRNA molecule may be formed by transcription from a nucleotide sequence which is substantially homologous to a nucleotide sequence consisting of SEQ ID NO:1; the complement of SEQ ID NO:1; SEQ ID NO:3, the complement of SEQ ID NO:3; SEQ ID NO:4; the complement of SEQ ID NO:4; SEQ ID NO:6, the complement of SEQ ID NO:6; SEQ ID NO:7; the complement of SEQ ID NO:7; SEQ ID NO:9, the complement of SEQ ID NO:9; a fragment of at least 19 contiguous nucleotides of SEQ ID NO:1, SEQ ID NO:3, SEQ ID NO:4, SEQ ID NO:6, SEQ ID NO:7, or SEQ ID NO:9 (e.g., SEQ ID NOs:10-15); the complement of a fragment of at least 19 contiguous nucleotides of SEQ ID NO:1, SEQ ID NO:3, SEQ ID NO:4, SEQ ID NO:6, SEQ ID NO:7, or SEQ ID NO:9; a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; the complement of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; the complement of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; a fragment of at least 19 contiguous nucleotides of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; the complement of a fragment of at least 19 contiguous nucleotides of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; a fragment of at least 19 contiguous nucleotides of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; and the complement of a fragment of at least 19 contiguous nucleotides of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9.

In particular embodiments, a recombinant DNA molecule encoding a dsRNA molecule may comprise at least two nucleotide sequence segments within a transcribed sequence, such sequences arranged such that the transcribed sequence comprises a first nucleotide sequence segment in a sense orientation, and a second nucleotide sequence segment (comprising the complement of the first nucleotide sequence segment) is in an antisense orientation, relative to at least one promoter, wherein the sense nucleotide sequence segment and the antisense nucleotide sequence segment are linked or connected by a spacer sequence segment of from about five (~5) to about one thousand (~1000) nucleotides.

The spacer sequence segment may form a loop between the sense and antisense sequence segments. The sense nucleotide sequence segment or the antisense nucleotide sequence segment may be substantially homologous to the nucleotide sequence of a target gene (e.g., a gene comprising SEQ ID NO:1, SEQ ID NO:3, SEQ ID NO:4, SEQ ID NO:6, SEQ ID NO:7, or SEQ ID NO:9) or fragment thereof (e.g., SEQ ID NOs:10-15). In some embodiments, however, a recombinant DNA molecule may encode a dsRNA molecule without a spacer sequence. In embodiments, a sense coding sequence and an antisense coding sequence may be different lengths.

Sequences identified as having a deleterious effect on pathogens or a plant-protective effect with regard to pathogens may be readily incorporated into expressed dsRNA molecules through the creation of appropriate expression cassettes in a recombinant nucleic acid molecule of the disclosure. For example, such sequences may be expressed as a hairpin with stem and loop structure by taking a first segment corresponding to a target gene sequence (e.g., SEQ ID NO:1, SEQ ID NO:3, SEQ ID NO:4, SEQ ID NO:6, SEQ ID NO:7, SEQ ID NO:9, and fragments thereof (e.g., SEQ ID NOs:10-15)); linking this sequence to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms and comprises the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native pathogen sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

V. Target Gene Suppression in a Plant Pathogen

A. Overview

In some embodiments of the disclosure, at least one nucleic acid molecule useful for the control of pathogens may be provided to a pathogen, wherein the nucleic acid molecule leads to RNA-mediated gene silencing in the pathogen. In particular embodiments, an iRNA molecule (e.g., dsRNA, siRNA, miRNA, shRNA, and hpRNA) may be provided to the pathogen. In some embodiments, a nucleic acid molecule useful for the control of pathogens may be provided to a pathogen by contacting the nucleic acid molecule with the pathogen. In these and further embodiments, a nucleic acid molecule useful for the control of pathogens may be provided by contact or on a feeding substrate of the pathogen. In these and further embodiments, a nucleic acid molecule useful for the control of pathogens may be provided through contact and/or uptake of plant material treated with the nucleic acid molecule that is contacted and/or uptaken by the pathogen.

B. RNAi-mediated Target Gene Suppression

In embodiments, the disclosure provides iRNA molecules (e.g., dsRNA, siRNA, miRNA, shRNA, and hpRNA) that may be designed to target essential native nucleotide sequences (e.g., essential genes) in the transcriptome of a pathogen (e.g., *Zymoseptoria tritici* and *Puccinia graminis* f. sp. *tritici*), for example by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the disclosure may be used in methods for gene suppression in a pathogen, thereby reducing the level or incidence of damage caused by the fungal pathogen on a plant. As used herein the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand". The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In embodiments of the disclosure, any form of iRNA molecule may be used. Those of skill in the art will understand that dsRNA molecules typically are more stable than are single-stranded RNA molecules, during preparation and during the step of providing the iRNA molecule to a cell, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a pathogen. In certain embodiments, the in vitro transcribed iRNA molecule may be a stabilized dsRNA molecule that comprises a stem-loop structure. After a pathogen contacts the in vitro transcribed iRNA molecule, post-transcriptional inhibition of a target gene in the pathogen (for example, an essential gene) may occur.

In some embodiments of the disclosure, expression of a nucleic acid molecule comprising at least 15 contiguous nucleotides of a nucleotide sequence is used in a method for post-transcriptional inhibition of a target gene in a pathogen, wherein the nucleotide sequence is selected from the group consisting of: SEQ ID NO:1; the complement of SEQ ID NO:1; SEQ ID NO:3; the complement of SEQ ID NO:3; SEQ ID NO:4; the complement of SEQ ID NO:4; SEQ ID NO:6; the complement of SEQ ID NO:6; SEQ ID NO:7; the complement of SEQ ID NO:7; SEQ ID NO:9; the complement of SEQ ID NO:9; a fragment of at least 15 contiguous nucleotides of SEQ ID NO:1, SEQ ID NO:3, SEQ ID NO:4, SEQ ID NO:6, SEQ ID NO:7, or SEQ ID NO:9 (e.g., SEQ ID NOs:10-15); the complement of a fragment of at least 15 contiguous nucleotides of SEQ ID NO:1, SEQ ID NO:3, SEQ ID NO:4, SEQ ID NO:6, SEQ ID NO:7, or SEQ ID NO:9; a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; the complement of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; the complement of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; a fragment of at least 15 contiguous nucleotides of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; the complement of a fragment of at least 15 contiguous nucleotides of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; a fragment of at least 15 contiguous nucleotides of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; and the complement of a fragment of at least 15 contiguous nucleotides of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a pathogen.

In some embodiments, expression of at least one nucleic acid molecule comprising at least 15 contiguous nucleotides of a nucleotide sequence may be used in a method for post-transcriptional inhibition of a target gene in a pathogen, wherein the nucleotide sequence is selected from the group consisting of: SEQ ID NO:1; the complement of SEQ ID NO:1; SEQ ID NO:3; the complement of SEQ ID NO:3; SEQ ID NO:4; the complement of SEQ ID NO:4; SEQ ID NO:6; the complement of SEQ ID NO:6; SEQ ID NO:7; the complement of SEQ ID NO:7; SEQ ID NO:9; the complement of SEQ ID NO:9; a fragment of at least 15 contiguous nucleotides of SEQ ID NO:1, SEQ ID NO:3, SEQ ID NO:4, SEQ ID NO:6, SEQ ID NO:7, or SEQ ID NO:9 (e.g., SEQ ID NOs:10-15); the complement of a fragment of at least 15 contiguous nucleotides of SEQ ID NO:1, SEQ ID NO:3, SEQ ID NO:4, SEQ ID NO:6, SEQ ID NO:7, or SEQ ID NO:9; a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; the complement of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; the complement of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; a fragment of at least 15 contiguous nucleotides of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; the complement of a fragment of at least 15 contiguous nucleotides of a native coding sequence of a *Zymoseptoria* organism comprising SEQ ID NO:1, SEQ ID NO:3, SEQ ID NO:4, SEQ ID NO:6, SEQ ID NO:7, or SEQ ID NO:9; a fragment of at least 15 contiguous nucleotides of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9; and the complement of a fragment of at least 15 contiguous nucleotides of a native non-coding sequence of a *Zymoseptoria* organism that is transcribed into a native RNA molecule comprising SEQ ID NO:1, SEQ ID NO:3, SEQ ID NO:4, SEQ ID NO:6, SEQ ID NO:7, or SEQ ID NO:9. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a pathogen. In particular examples, such a nucleic acid molecule may comprise a nucleotide sequence comprising SEQ ID NO:1, SEQ ID NO:3, SEQ ID NO:4, SEQ ID NO:6, SEQ ID NO:7, or SEQ ID NO:9.

In some embodiments of the disclosure, the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present disclosure is sequence-specific; i.e., nucleotide sequences substantially homologous to the iRNA molecule(s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 15, 16, 17, 18, 19, 20, 21, 22, 23, 24, 25, 26, 27, 28, 29, 30, 35, 40, 45, 25, 50, 100, 200, 300, 400, 500, or at least about 1000 bases. In some embodiments, a sequence of greater than 15 to 100 nucleotides may be used. In particular embodiments, a sequence of greater than about 200 to 300 nucleotides may be used. In particular embodiments, a sequence of greater than about 500 to 1000 nucleotides may be used, depending on the size of the target gene.

In certain embodiments, expression of a target gene in a pathogen may be inhibited by at least 10%; at least 33%; at least 50%; or at least 80% within a cell of the pathogen, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although in certain embodiments of the disclosure inhibition occurs in substantially all cells of the pathogen, in other embodiments inhibition occurs only in a subset of cells expressing the target gene.

In some embodiments, transcriptional suppression in a cell is mediated by the presence of a dsRNA molecule exhibiting substantial sequence identity to a promoter DNA sequence or the complement thereof, to effect what is referred to as "promoter trans suppression". Gene suppression may be effective against target genes in a pathogen that may uptake or contact such dsRNA molecules, for example, by uptaking or contacting plant material containing the dsRNA molecules. dsRNA molecules for use in promoter trans suppression may be specifically designed to inhibit or suppress the expression of one or more homologous or complementary sequences in the cells of the pathogen. Post-transcriptional gene suppression by antisense or sense oriented RNA to regulate gene expression in plant cells is disclosed in U.S. Pat. Nos. 5,107,065; 5,231,020; 5,283,184; and 5,759,829.

C. Expression of iRNA Molecules Provided to a Plant Pathogen

Expression of iRNA molecules for RNAi-mediated gene inhibition in a pathogen may be carried out in any one of many in vitro or in vivo formats. The iRNA molecules may then be provided to a pathogen, for example, by contacting the iRNA molecules with the pathogen, or by causing the pathogen to uptake or otherwise internalize the iRNA molecules. Some embodiments of the disclosure include transformed host plants of a pathogen, transformed plant cells, and progeny of transformed plants. The transformed plant cells and transformed plants may be engineered to express one or more of the iRNA molecules, for example, under the control of a heterologous promoter, to provide a protective effect. Thus, when a transgenic plant or plant cell is consumed by a pathogen during feeding, this pathogen may uptake iRNA molecules expressed in the transgenic plants or cells. The nucleotide sequences of the present disclosure may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a pathogen comprises providing in the tissue of the host a gene-suppressive amount of at least one dsRNA molecule formed following transcription of a nucleotide sequence as described herein, at least one segment of which is complementary to an mRNA sequence within the cells of the pathogen. A dsRNA molecule, including its modified form such as an siRNA, miRNA, shRNA, or hpRNA molecule, contacted or uptaken by a pathogen in accordance with the disclosure, may be at least from about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or 100% identical to an RNA molecule transcribed from a nucleic acid molecule comprising a nucleotide sequence comprising SEQ ID NO:1, SEQ ID NO:3, SEQ ID NO:4, SEQ ID NO:6, SEQ ID NO:7, or SEQ ID NO:9. Isolated and substantially purified nucleic acid molecules including, but not limited to, non-naturally occurring nucleotide sequences and recombinant DNA constructs for providing dsRNA molecules of the present disclosure are therefore provided, which suppress or inhibit the expression of an endogenous coding sequence or a target coding sequence in the pathogen when introduced thereto.

Particular embodiments provide a delivery system for the delivery of iRNA molecules for the post-transcriptional inhibition of one or more target gene(s) in a plant pathogen and control of a population of the pathogen. In some embodiments, the delivery system comprises contact and/or uptake of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the disclosure. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the disclosure (e.g., a stabilized dsRNA molecule); to transform a plant cell or plant; and to generate the transgenic plant cell or the transgenic plant that contains the transcribed iRNA molecule.

To impart pathogen resistance to a transgenic plant, a recombinant DNA molecule may, for example, be transcribed into an iRNA molecule, such as a dsRNA molecule, an siRNA molecule, an miRNA molecule, an shRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a pathogen of a type that may infect the host plant. Expression of a target gene within the pathogen is suppressed by the uptaken dsRNA molecule, and the suppression of expression of the target gene in the pathogen results in, for example, cessation of feeding by the pathogen, with an ultimate result being, for example, that the transgenic plant is protected from further damage by the pathogen. The modulatory effects of dsRNA molecules have been shown to be applicable to a variety of genes expressed in fungal pathogens, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present disclosure, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a wheat plant) caused by a pathogen that infects the plant, wherein the method comprises providing on the host plant a dsRNA comprising at least one nucleic acid molecule of the disclosure, wherein the nucleic acid molecule(s) functions upon being taken up by the pathogen to inhibit the expression of a target sequence within the pathogen, which inhibition of expression results in mortality, reduced growth, and/or reduced reproduction of the pathogen, thereby reducing the damage to the host plant caused by the pathogen. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a pathogen cell. In some embodiments, the nucleic acid molecule(s) consist of one nucleotide sequence that is specifically hybridizable to a nucleic acid molecule expressed in a pathogen cell.

In other embodiments, a method for improving the yield of a wheat crop is provided, wherein the method comprises introducing into a wheat plant at least one nucleic acid molecule of the disclosure; cultivating the wheat plant to allow the expression of an iRNA molecule comprising the nucleic acid sequence, wherein expression of an iRNA molecule comprising the nucleic acid sequence inhibits pathogen growth and/or pathogen damage, thereby reducing or eliminating a loss of yield due to pathogen infection. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a pathogen cell. In some embodiments, the nucleic acid molecule(s) consists of one nucleotide sequence that is specifically hybridizable to a nucleic acid molecule expressed in a pathogen cell.

In some embodiments, a method for modulating the expression of a target gene in a pathogen is provided, the method comprising: transforming a plant cell with a vector comprising a nucleic acid sequence encoding at least one nucleic acid molecule of the disclosure, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the pathogen. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a pathogen cell. In some embodiments, the nucleic acid molecule(s) consists of one nucleotide sequence that is specifically hybridizable to a nucleic acid molecule expressed in a pathogen cell. In other embodiments, a vector can comprise at least one strand of a double-stranded nucleic acid.

iRNA molecules of the disclosure can be incorporated within parts of a plant. For example, iRNA molecules can be incorporated within the seeds of a plant species (e.g., wheat), either as a product of expression from a recombinant gene incorporated into a genome of the plant cells, or as incorporated into a coating or seed treatment that is applied to the seed before planting. Alternatively, naked dsRNA and/or a plasmid expressing a dsRNA hairpin or equivalent can be incorporated within a plant part (e.g., a seed). iRNA molecules, naked dsRNA, and/or a plasmid expressing a dsRNA hairpin or equivalent can be adapted for uptake by a plant part (e.g., a root system). Also included in embodiments of the disclosure are delivery systems for the delivery of iRNA molecules to pathogens. For example, the iRNA molecules of the disclosure may be directly introduced into the cells of a pathogen. Methods for introduction may include direct mixing of iRNA with plant tissue from a host for the pathogen, as well as application of compositions comprising iRNA molecules of the disclosure to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the pathogen known to infect the plant. iRNA molecules produced by chemical or enzymatic synthesis may also be formulated in a manner consistent with common agricultural practices, and used as spray-on products for controlling plant damage by a pathogen. The formulations may include the appropriate stickers and wetters required for efficient foliar coverage, as well as UV protectants to protect iRNA molecules (e.g., dsRNA molecules) from UV damage. Such additives are commonly used in the biopesticide industry, and are well known to those skilled in the art. Such applications may be combined with other spray-on fungicide applications (biologically based or otherwise) to enhance plant protection from pathogen. Fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dipymetitrone, dithianon, dodemorph, dodemorph acetate, dodine, dodine free base, edifenphos, enestrobin, enestroburin, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, fluindapyr, flumorph, fluopicolide, fluopyram, fluoroimide, fluoxastrobin, fluquinconazole, flusilazole, flusulfamide, flutianil, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isofetamide, isoprothiolane, isopyrazam, isotianil, kasugamycin, kasugamycin hydrochloride hydrate, kresoxium-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, pydiflumetofen, pyrametostrobin, pyraoxystrobin, pyraziflumid, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1 dsDNA Sample Preparation

SdhB (SEQ ID NO:1), SdhB (SEQ ID NO:3), SdhC (SEQ ID NO:4), SdhC (SEQ ID NO:6), SdhD (SEQ ID NO:7), and SdhD (SEQ ID NO:9) were synthesized and produced by a third party manufacturer (AgroRNA, Seoul, Korea).

Example 2

Identification of Candidate Target Genes

Sdh is a gene that encodes the only enzyme involved in both the citric acid cycle and the electron transport chain. Sdh has gene subunits, which include but are not limited to gene subunits B (SdhB), C (SdhC), D (SdhD). The SDH enzyme also catalyzes the oxidation of succinate to fumarate in the mitochondria matrix and transfers electrons to ubiquinone without pumping protons across the mitochondrial inner membrane. (Shaobai Huang, A Harvey Millar, Succinate dehydrogenase: the complex roles of a simple enzyme, Current Opinion in Plant Biology, Volume 16, Issue 3, June 2013, Pages 344-349, ISSN1369-5266). The gene and coding sequences of SdhB, SdhC, and SdhD from *Zymoseptoria tritici* was retrieved from GENBANK (Accession Number: XM_003850705.1; XM_003850403.1; and XM_003853561.1) respectively.

A candidate target gene encoding *Zymoseptoria* SdhB, SdhC, and SdhD (SEQ ID NO:1, SEQ ID NO:3, SEQ ID NO:4, SEQ ID NO:6, SEQ ID NO:7, and SEQ ID NO:9) was identified as a gene that may lead to pathogen mortality, inhibition of growth, inhibition of development, or inhibition of reproduction.

The *Zymoseptoria* sequences SEQ ID NO:1, SEQ ID NO:3, SEQ ID NO:4, SEQ ID NO:6, SEQ ID NO:7, and SEQ ID NO:9 are provided in public databases. The *Zymoseptoria* SdhB, SdhC, and SdhD sequences (SEQ ID NO:1, SEQ ID NO:3, SEQ ID NO:4, SEQ ID NO:6, SEQ ID NO:7, and SEQ ID NO:9) are related to a sequence from *Mycosphaerella graminicola* (GENBANK Accession Nos.: XM_003850705.1; XM_003850403.1; and XM_003853561.1). The *Septoria* SDHB, SDHC, and SDHD amino acid sequences (SEQ ID NO:2; SEQ ID NO:5; SEQ ID NO:8) are *Zymoseptoria tritici* proteins having GENBANK Accession Nos. XP_003850753.1; XP_003850451.1; XP_003853609.1, respectively. (100% similar; 100% identical over the homology region).

Full-length or partial clones of sequences of a *Zymoseptoria* candidate gene, herein referred to as Sdh, SdhB, SdhC, and/or SdhD, were used to generate PCR amplicons for dsRNA synthesis.

SEQ ID NO:1 shows a 1247 bp DNA sequence of *Zymoseptoria* SdhB.

SEQ ID NO:3 shows a 894 bp DNA sequence of *Zymoseptoria* SdhB (mRNA).

SEQ ID NO:4 shows a 721 bp DNA sequence of *Zymoseptoria* SdhC.

SEQ ID NO:6 shows a 564 bp DNA sequence of *Zymoseptoria* SdhB (mRNA).

SEQ ID NO:7 shows a 750 bp DNA sequence of *Zymoseptoria* SdhD.

SEQ ID NO:9 shows a 582 bp DNA sequence of *Zymoseptoria* SdhD (mRNA).

SEQ ID NO:10 shows a 250 bp DNA sequence of *Zymoseptoria* SdhB-T1

SEQ ID NO:11 shows a 250 bp DNA sequence of *Zymoseptoria* SdhB-T2

SEQ ID NO:12 shows a 250 bp DNA sequence of *Zymoseptoria* SdhC-T1

SEQ ID NO:13 shows a 250 bp DNA sequence of *Zymoseptoria* SdhC-T2

SEQ ID NO:14 shows a 250 bp DNA sequence of *Zymoseptoria* SdhD-T1

SEQ ID NO:15 shows a 250 bp DNA sequence of *Zymoseptoria* SdhD-T2

Example 3

Efficacy of Candidate Target Genes

Synthetic dsRNA designed to inhibit target gene sequences identified in EXAMPLE 2 caused inhibition of disease severity when administered to *Zymoseptoria* in bioassays. SDHB-T1 and SDHB-T2 were observed to control *Septoria* leaf blotch on wheat seedlings when compared to the non-treated control.

TABLE 2

Compound formulation in 4-fold dilutions (15 mL) for each treatment. Treatments 1-3 were a combination of tiles SDHB-T1 and SDHB-T2 (1:1 ratio); treatments 4-6 were SDHB-T1; treatments 7-9 were SDHB-T2; treatments 10-12 were a combination of tiles SDHC-T1 and SDHC-T2; treatments 13-15 were SDHC-T1; treatments 16-18 were SDHC-T2; treatments 19-21 were a combination of tiles SDHD-T1 and SDHD-T2; treatments 22-24 were SDHD-T1; treatments 25-27 were SDHD-T2; treatments 28-30 were a combination of tiles SDHB-T1, SDHC-T1, and SDHD-T1; treatments 31-33 were a combination of SDHB-T2, SDHC-T2, and SDHD-T2; and treatments 34-36 were a dsRNA negative control for YFP protein.

| Rates (ppm) | Spray Volume (mL) | dsRNA material (mg) |
|---|---|---|
| 200 | 15 | 3.000 |
| 50 | 15 | 0.750 |
| 12.5 | 15 | 0.188 |

RNAi (dsRNA) fungicidal solutions were prepared in TE buffer (pH 8.0), which were then mixed with 9 volumes of phosphate buffer (pH 7.5) containing an adjuvant. The fungicidal solutions were applied to wheat seedlings using an automated booth sprayer to run-off. All sprayed plants were allowed to air dry prior to further handling.

The following served as controls: adjuvant in phosphate buffer control, disease pressure control (untreated), and clean plant control (negative control).

These plants were inoculated with an aqueous spore suspension of *Zymoseptoria tritici* either prior to or after fungicidal treatments. After inoculation the plants were kept in 100% relative humidity for 3 days to allow spores to germinate and infect the leaves. The plants were then transferred to a greenhouse set at 20° C. until disease developed.

TABLE 3

Results of percentage of disease control of Sdh dsRNA foliar application bioassays obtained with *Zymoseptoria tritici* after 3 days curative and 1 day protectant.

| | | | Disease Control (%) | |
|---|---|---|---|---|
| TRT | Tiles | Rate (ppm) | SEPTTR-AR 3DC | SEPTTR-AR 1DP |
| 1 | SDHB* | 200 | 81 | 25 |
| 2 | (SDHB-T1, | 50 | 85 | 25 |
| 3 | SDHB-T2) | 12.5 | 85 | 25 |
| 4 | SDHB-T1 | 200 | 95 | 50 |
| 5 | | 50 | 95 | 21 |
| 6 | | 12.5 | 94 | 21 |
| 7 | SDHB-T2 | 200 | 85 | 23 |
| 8 | | 50 | 77 | 19 |
| 9 | | 12.5 | 73 | 19 |
| 10 | SDHC* | 200 | 25 | 21 |
| 11 | (SDHC-T1, | 50 | 17 | 21 |
| 12 | SDHC-T2) | 12.5 | 17 | 21 |
| 13 | SDHC-T1 | 200 | 60 | 17 |
| 14 | | 50 | 56 | 17 |
| 15 | | 12.5 | 31 | 17 |
| 16 | SDHC-T2 | 200 | 40 | 17 |
| 17 | | 50 | 15 | 15 |
| 18 | | 12.5 | 15 | 15 |
| 19 | SDHD* | 200 | 60 | 25 |
| 20 | (SDHD-T1, | 50 | 44 | 25 |
| 21 | SDHD-T2) | 12.5 | 44 | 25 |
| 22 | SDHD-T1 | 200 | 48 | 21 |
| 23 | | 50 | 38 | 21 |
| 24 | | 12.5 | 35 | 15 |
| 25 | SDHD-T2 | 200 | 56 | 21 |
| 26 | | 50 | 46 | 21 |
| 27 | | 12.5 | 44 | 21 |
| 28 | SDH-1 | 200 | 63 | 21 |
| 29 | (SDHB-T1, | 50 | 29 | 21 |
| 30 | SDHC-T1, SDHD-T1) | 12.5 | 13 | 21 |
| 31 | SDH-2 | 200 | 67 | 0 |
| 32 | (SDHB-T2, | 50 | 44 | 0 |
| 33 | SDHC-T2, SDHD-T2) | 12.5 | 27 | 0 |
| 34 | YFP | 200 | 17 | 8 |
| 35 | | 50 | 8 | 8 |
| 36 | | 12.5 | 0 | 0 |
| 37 | Triton X-100 + buffer | N/A | 0 | 0 |
| 38 | TE + Phosphate buffer | NA | 0 | 0 |
| 39 | Disease Pressure | NA | 0 | 0 |
| 40 | Clean Plant | NA | 100 | 100 |

Replicated bioassays demonstrated that uptake of dsRNA preparations derived from Sdh resulted in control of *Zymoseptoria tritici.*

Example 4

Methods for Analysis of Transgenic Plants

DNA extraction is carried out on leaf samples using "DNAeasy Plant Mini Kit" following manufacturer's instructions (Qiagen Inc., Valencia, Calif. USA) and PCR is carried out for selectable marker nptII using PCR. A fragment is amplified using forward and reverse primers using the following thermal cycle conditions: 94° C. for 30 s, 55° C. for 30 s, 72° C. for 60 s for 40 cycles with a final extension at 72° C. for 10 min.

Analysis of $T_0$ Transgenic Plants—Southern Hybridization Method

Wheat genomic DNA is extracted from transgenic wheat by standard methods. Approximately 15 mu.g of DNA is digested overnight with BamHI and separated by 0.8% agarose gel electrophoresis (Sambrook, 2001) and the DNA is transferred onto a nylon membrane (Pall Biodyne® B), followed by standard hybridization procedures (Sambrook 2001). The Stargate3 amplicon is labeled as probe using [.alpha.-32 P] dCTP (NEN) using the multiprime system (Amersham, Ill. USA), X-Ray film is exposed to the blots at −80° C.

Analysis of $T_1$ Transgenic Plants—Genomic PCR Method $T_1$ seeds of each transgenic event are kept on moist filter paper in petri plates for 3-4 days and the germinated seeds are transferred to pots. Approximately a three centimeter-long young leaf is collected from each plant and frozen dried. Genomic DNA is extracted in DNA extraction buffer containing 0.1M Tris-HCL, pH 8.0, 0.05M EDTA pH 8.0, 1.25% SDS. Primers are designed against the two extremes of the hairpin construct.

The PCR reaction is performed in a Thermalcycler with the following protocol: 95° C. for 15 min; (94° C. for 1 min; 63° C. (stargate1)/65° C. (stargate3) for 45 seconds; 72° C. for 1 min) times 35 cycles and final extension of 10 minutes at 72° C. Two amplicons are used in the study to assay for both ends of the hpRNA transgene including a large portion of the promoter.

Analysis of $T_1$ Transgenic Plants—Virus Bioassay Method

Virus inoculum is prepared by grinding wheat streak mosaic virus (WSMV) infected tissue in a mortar and pestle at a 1:10 w/v ratio in 0.02 M Potassium phosphate buffer (pH 7). The homogenate is filtered through four layers of Miracloth® (Calbiochem, USA), abrasive Celite (Johns-Manville, USA) is added at 2% w/v to a final volume of inoculum, and the mixture is left on ice for one hour. Putative transgenic BW26 plants are doubly inoculated at the 2-3 leaf stage, with the sap extracts from WSMV-infected leaf material. The sap plus celite abrasive is first applied with an air-powered spray gun and then leaves are gently rubbed with gloved fingers to ensure the infection of the plant by the virus. The plants are scored for symptoms at 14 dpi on a scale of 0-4 with 0 as healthy, 1 as mild with very few streaks, 2 as moderate with streaks that coalesce, 3 as severe with approximately 50 percent leaf area with streaks, 4 as the most severe or lethal symptoms where the streaks develop into chlorosis of more than 70 percent of leaf area. Samples are collected for WSMV-specific ELISA using Agdia reagents (Elkhart, Ind.) following manufacturer's instructions. Plates are read at A405 nm in ELISA Reader Spectra Max 340 PC (Molecular Devices, CA USA) 60 minutes after addition of substrates. Healthy controls are included on every plate, every sample is duplicated, and means are used in calculating the ELISA value ratio between inoculated and healthy controls. Data is also recorded on the fertility and height of plants.

Detection of WSMV Particles and RNA from Inoculated Transgenic Lines

Total RNA is extracted from WSMV inoculated transgenic plants using a Qiagen RNAeasy mini kit following the manufacturer's instructions. 500 ng total RNA is serially diluted in 1:10 steps to 5 pg (final dilution 10-5). In order to amplify viral RNA but avoid amplifying transcripts from the transgene, primers are designed to hybridize to sequences just outside the cloned NIa sequence used in the transgene. The primers used are NIa-1F SEQ ID NO:31 5'-CTGGACCGATCGGATTAAGA-3' and NIa-3R SEQ ID NO:32 5'-CTGAGAACTTCCATGGCACA-3'. Reverse transcription (RT) reaction is carried out at 50° C. for 30 min, following by 95° C. for 15 min; (94° C. for 1 min; 60° C. for 45 seconds; 72° C. for 1 min) times 35 cycles and final extension of 10 minutes at 72° C.

Test-Inoculation to Detect Infectious Virus in Leaf Sap

Sap is extracted from inoculated transgenic plants at 28 dpi using 0.02 M potassium phosphate buffer; the initial concentration is 1:10 (w leaf/v buffer). This is further diluted to 1:250 and 1:500 concentrations. Each dilution is mixed with celite abrasive and then inoculated onto three plants each. This method is used to evaluate the effectiveness of the hpRNA construct in eliminating viral replication and preventing the formation of infectious particles. Symptoms are scored and leaf samples collected 14 dpi for ELISA as described previously.

Segregation Analysis of NIa Transgene and Resistance in Selected $T_1$ Families

Twenty five to 35 seeds from four selected transgenic lines are germinated in pots. Leaf samples are collected and DNA is extracted as described above. Genomic PCR is carried out to detect both Stargate 1 and Stargate 3 amplicons, to ensure the presence of the complete transgene promoter and hairpin construct. In order to observe if resistance co-segregated with the transgene, the plants are inoculated with WSMV, ELISA is performed 14 dpi on inoculated plants, plant heights and symptoms are recorded. Segregation of selectable marker nptII is also determined using PCR.

Example 5

Molecular and Serological Characterization of Transgenic Wheat

An initial assessment of $T_1$ individuals will indicate the presence of the selectable marker nptII via genomic PCR, verifying that these plants are transgenic. Further analysis involves inoculating each individual plant with *Zymoseptoria* and assaying with ELISA at 14 days post inoculation (dpi). As the disease progresses affected plants will appear retarded and show a general yellow mottling. Diseased plants are usually yellowed and moderately to severely stunted with prostrated tillers often with empty spikes or spikes with shriveled kernels.

Virus accumulation in leaves is determined using ELISA and expressed as a ratio of the average ELISA value for samples from the inoculated plants relative to the ELISA value for samples from the non-inoculated controls. This is done since the ELISA value for non-inoculated controls gave a low, background reading above zero using the Agdia kit.

The RNAi Construct Conferring Immunity Against *Zymoseptoria* in Wheat

The absence of symptoms in inoculated transgenic individuals from some transgenic events will lead to the hypothesis that they are immune. Experiments are conducted to see if infectious virus or viral RNA could be recovered from resistant inoculated transgenic plants. Leaf sap from plants in four transgenic inoculated families is extracted and inoculated onto test plants of control BW26 at various dilutions to investigate the presence of any infectious disease particles.

What may be claimed is:

1. A double-stranded nucleic acid comprising a ribonucleic acid (RNA) molecule consisting of at least 19 nucleotides, wherein the double-stranded nucleic acid is specifically hybridizable with a polynucleotide selected from the group consisting of:
   (a) a polynucleotide sequence of SEQ ID NO:10 and the complement of SEQ ID NO:10; and,
   (b) a polynucleotide sequence of SEQ ID NO:11 and the complement of SEQ ID NO:11.

2. The double-stranded nucleic acid of claim 1, wherein the polynucleotide sequence inhibits or down regulates the expression of an sdh gene endogenous nucleotide sequence specifically complementary to the polynucleotide sequence.

3. The double-stranded nucleic acid of claim 1, wherein contacting the polynucleotide sequence with a plant pathogen kills or inhibits the growth, reproduction, and/or feeding of the plant pathogen.

4. The plant pathogen of claim 3, wherein the plant pathogen is selected from the group consisting of *Zymoseptoria tritici*; *Zymoseptoria citri*; *Zymoseptoria caryae*; *Zymoseptoria curcurbitacearum*; *Zymoseptoria dianthi*; *Zymoseptoria glycines*; *Zymoseptoria helianthi*; *Zymoseptoria ostryae*; *Puccinia triticina*; *Puccinia striiformis*; *Phaeosphaeria nodorum*; *Rhyncosporium commune*; *Alternaria solani*; *Cercospora beticola*; *Magnaporthe grisea*; *Venturia inaequalis*; and *Phakopsora pachyrhizi*.

5. The double-stranded nucleic acid of claim 1, wherein the polynucleotide sequence is operably linked to a heterologous promoter.

6. The double-stranded nucleic acid of claim 1, wherein the polynucleotide sequence folds back and hybridizes to the complement thereof to form the double stranded molecule.

7. The double-stranded nucleic acid of claim 6, wherein the double stranded molecule is from 19 to 30 nucleotides in length.

8. The double-stranded nucleic acid of claim 1, wherein the double-stranded nucleic acid is incorporated into a plasmid vector.

9. The double-stranded nucleic acid of claim 1, wherein the double-stranded nucleic acid is provided as an oligonucleotide.

10. A composition comprising the double-stranded nucleic acid of claim 1.

11. A plant comprising the double-stranded nucleic acid of claim 1.

12. The plant of claim 11, wherein the plant is a monocot plant or a dicot plant.

13. The plant of claim 11, wherein the plant is a wheat plant.

14. The plant of claim 11, wherein the double-stranded nucleic acid is expressed in the plant as a ribonucleic acid molecule, and the ribonucleic acid molecule inhibits or down regulates the expression of a sdh gene endogenous nucleotide sequence specifically complementary to the polynucleotide sequence.

15. A method of making a transgenic plant cell capable of expressing a double-stranded nucleic acid comprising a ribonucleic acid (RNA) molecule that inhibits an sdh gene in a fungal species, said method comprises the steps of transforming a plant cell with the double-stranded nucleic acid of claim 1, wherein said double-stranded nucleic acid of claim 1 inhibits the sdh gene in the fungal species.

16. A method of controlling a fungus or oomycete, comprising providing to said fungus or oomycete the double-stranded nucleic acid of claim 1, or a composition comprising at least the double-stranded nucleic acid of claim 1.

* * * * *